United States Patent [19]
Kriesel

[11] Patent Number: 5,354,278
[45] Date of Patent: * Oct. 11, 1994

[54] FLUID DISPENSER

[75] Inventor: Marshall S. Kriesel, Bloomington, Minn.

[73] Assignee: Science Incorporated, Bloomington, Minn.

[*] Notice: The portion of the term of this patent subsequent to Nov. 23, 2010 has been disclaimed.

[21] Appl. No.: 53,723

[22] Filed: Apr. 26, 1993

Related U.S. Application Data

[63] Continuation-in-part of Ser. No. 870,521, Apr. 17, 1992, Pat. No. 5,263,940.

[51] Int. Cl.⁵ .................................. A61M 37/00
[52] U.S. Cl. ....................................... 604/132
[58] Field of Search .............. 604/132, 131, 93, 82, 604/83, 84, 85, 92; 128/DIG. 12

[56] References Cited

U.S. PATENT DOCUMENTS

| | | |
|---|---|---|
| Re. 26,488 | 11/1968 | Bull . |
| 3,189,231 | 6/1965 | Kibbel, Jr. et al. . |
| 3,235,138 | 2/1966 | Bull . |
| 3,244,326 | 4/1966 | Bull, Jr. . |
| 3,445,043 | 5/1969 | Bull . |
| 3,468,308 | 9/1969 | Bierman ............... 604/132 X |
| 3,469,578 | 9/1969 | Bierman ............... 604/246 X |
| 4,193,513 | 3/1980 | Bull, Jr. . |
| 4,337,769 | 7/1982 | Olson . |
| 4,379,453 | 4/1983 | Baron . |
| 4,857,055 | 8/1989 | Wang . |
| 4,994,031 | 2/1991 | Theeuwes ............... 604/85 |
| 5,122,116 | 6/1992 | Kriesel .................. 604/89 |
| 5,205,820 | 4/1993 | Kriesel ............. 128/DIG. 12 |
| 5,236,418 | 8/1993 | Kriesel .................. 604/85 |

*Primary Examiner*—Gene Mancene
*Assistant Examiner*—Jeffrey A. Smith
*Attorney, Agent, or Firm*—J. E. Brunton

[57] ABSTRACT

An elastomeric bladder type infusion device for delivering a beneficial agent, such as a drug to a patient at substantially a constant rate. The device uniquely includes an internally disposed functional substrate which carries the beneficial agent so that it can be mixed with the fluid as the fluid is being introduced into the device to distend the bladder to make it an energy source for controllably dispensing the solution mixture to a patient.

39 Claims, 15 Drawing Sheets

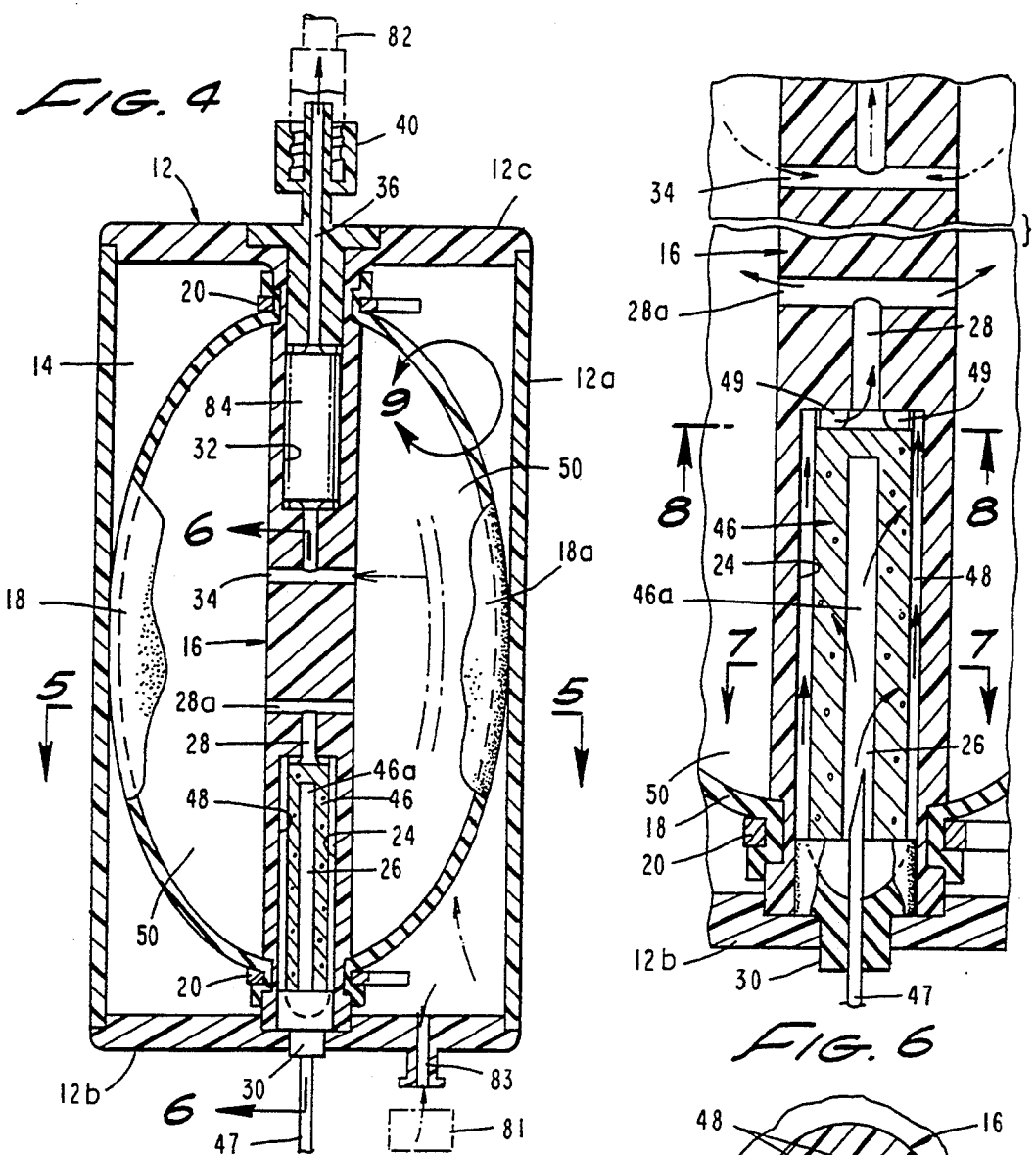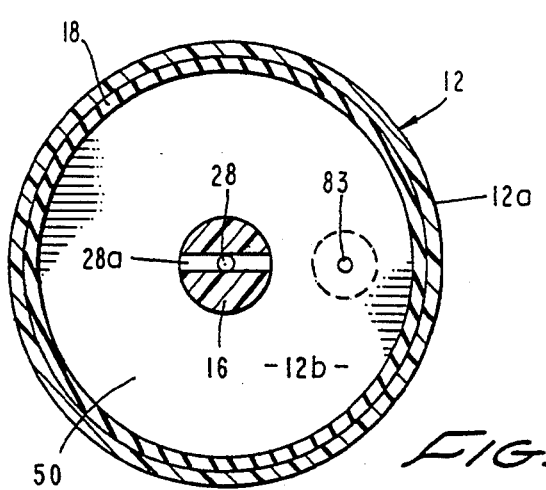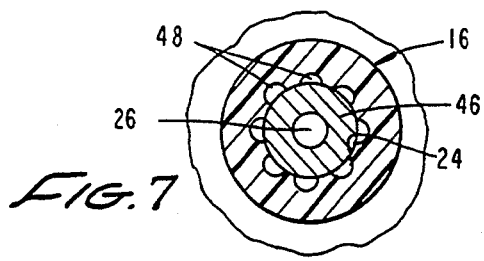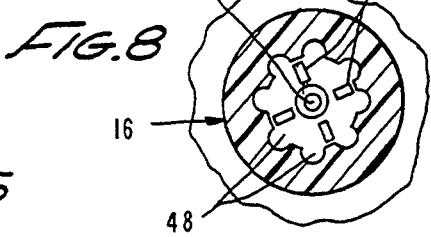

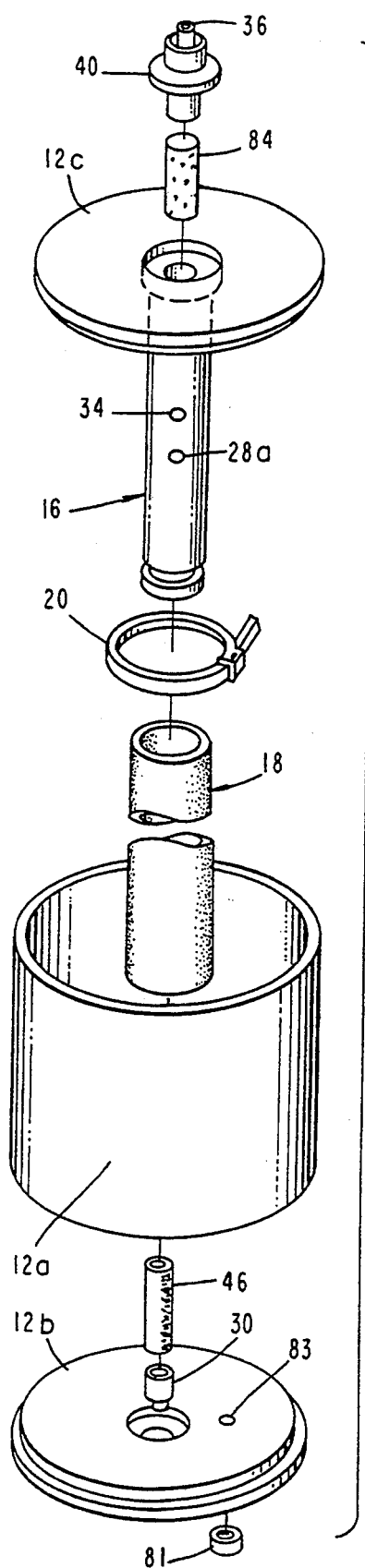
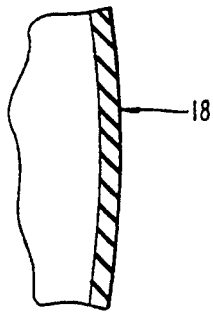
FIG. 9
FIG. 10
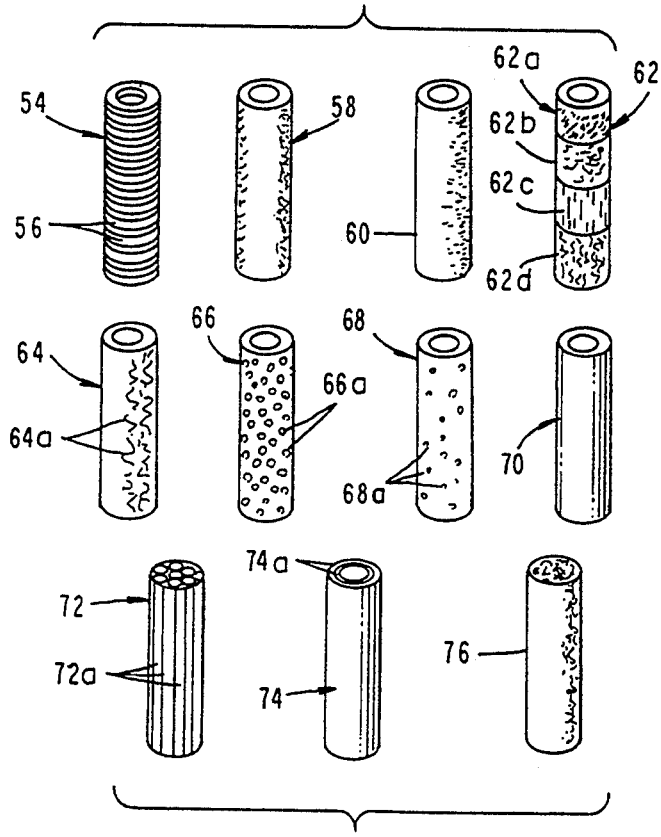
FIG. 11

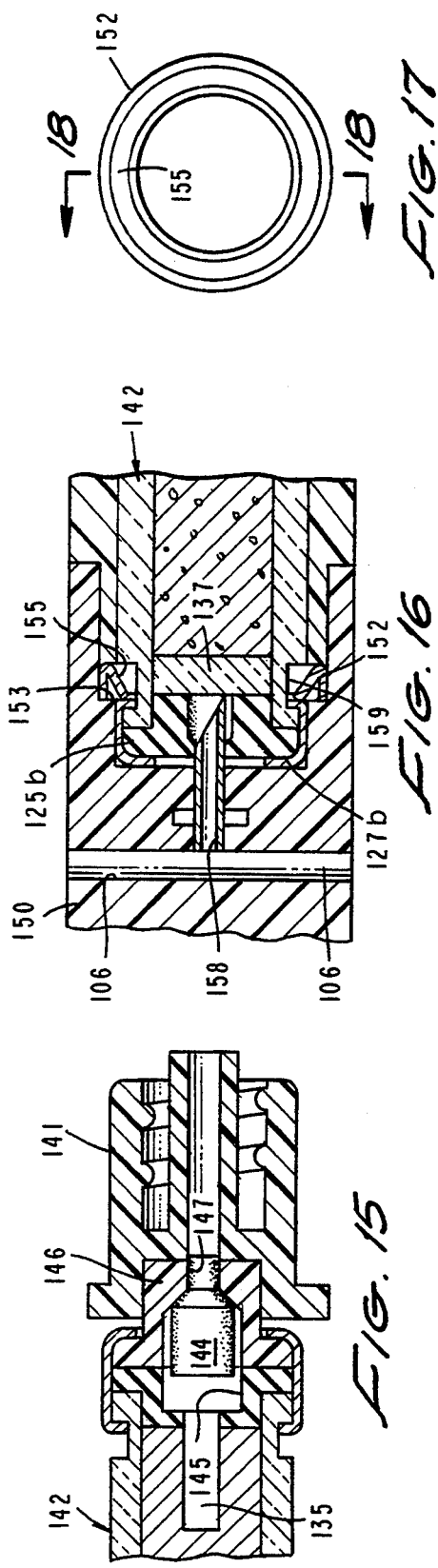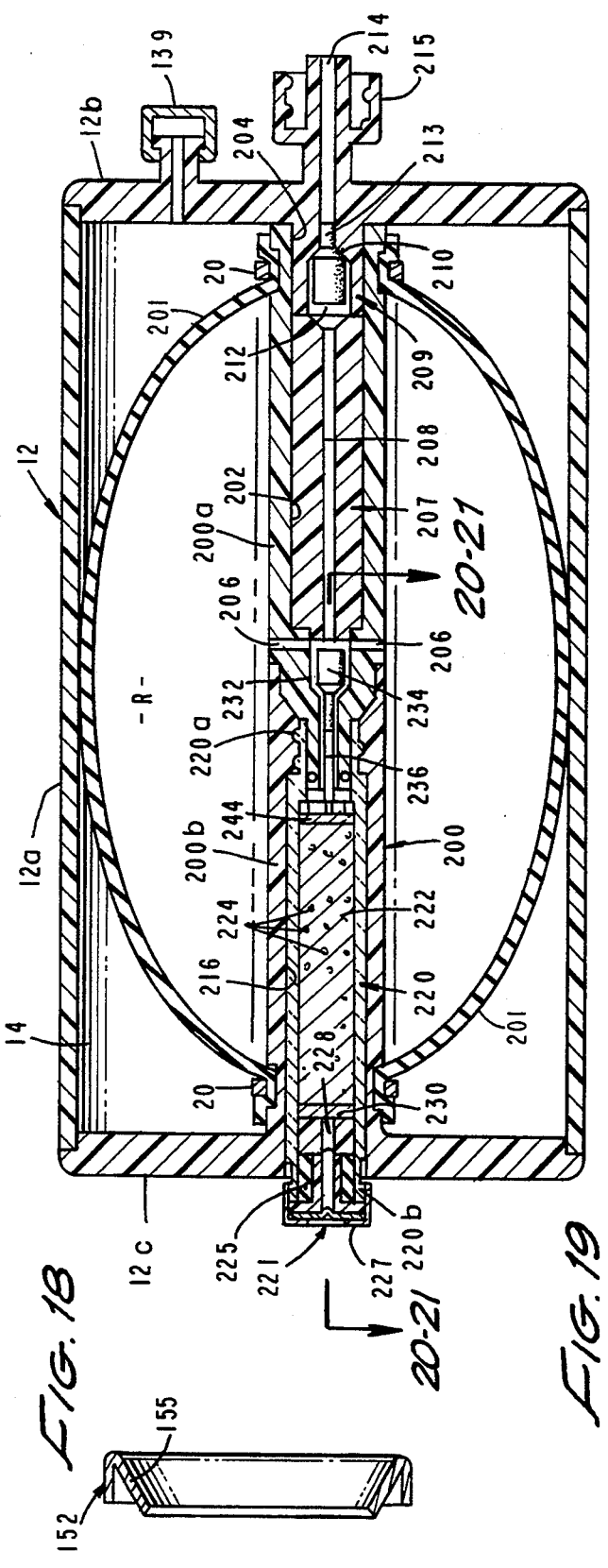

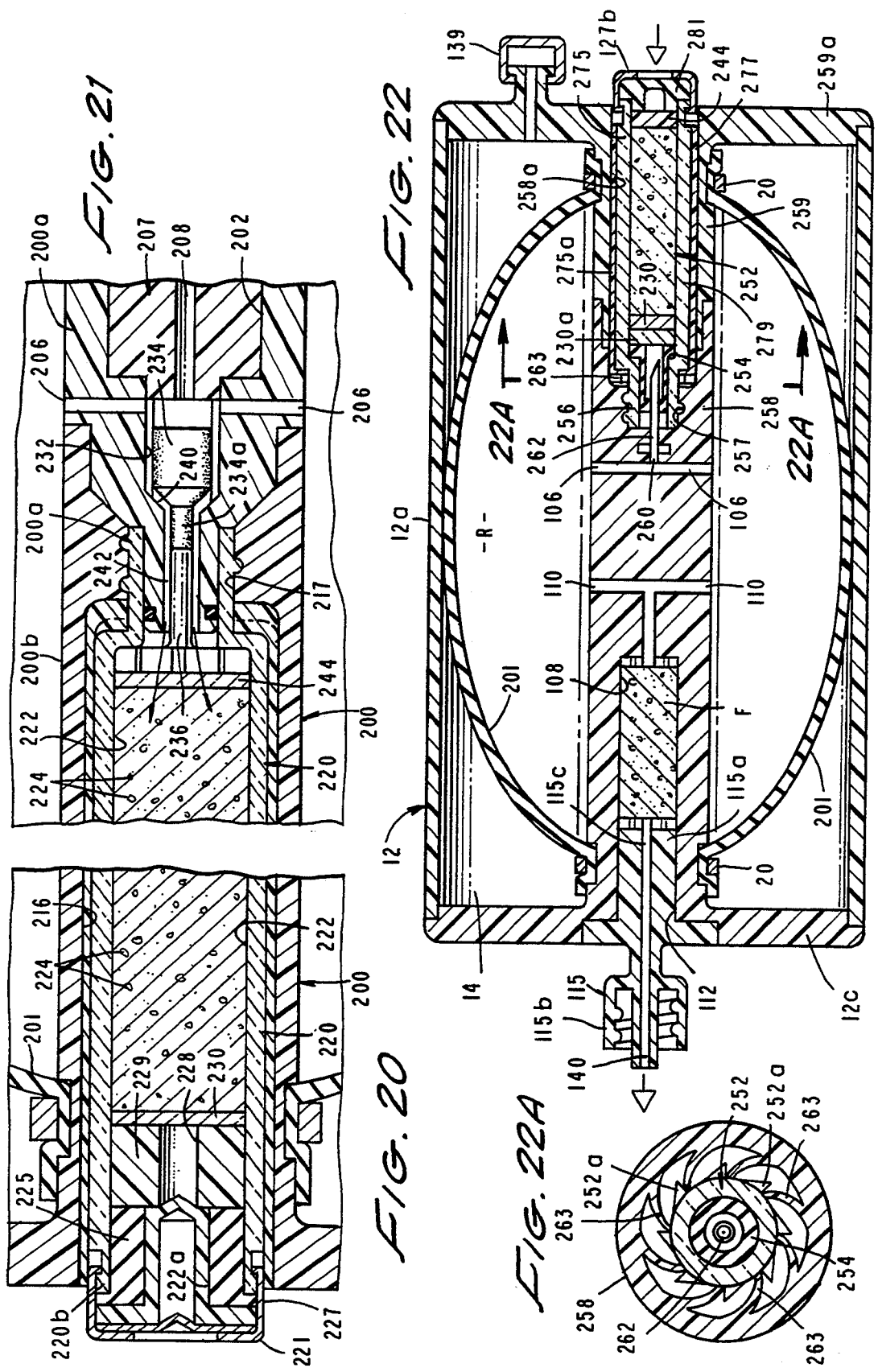

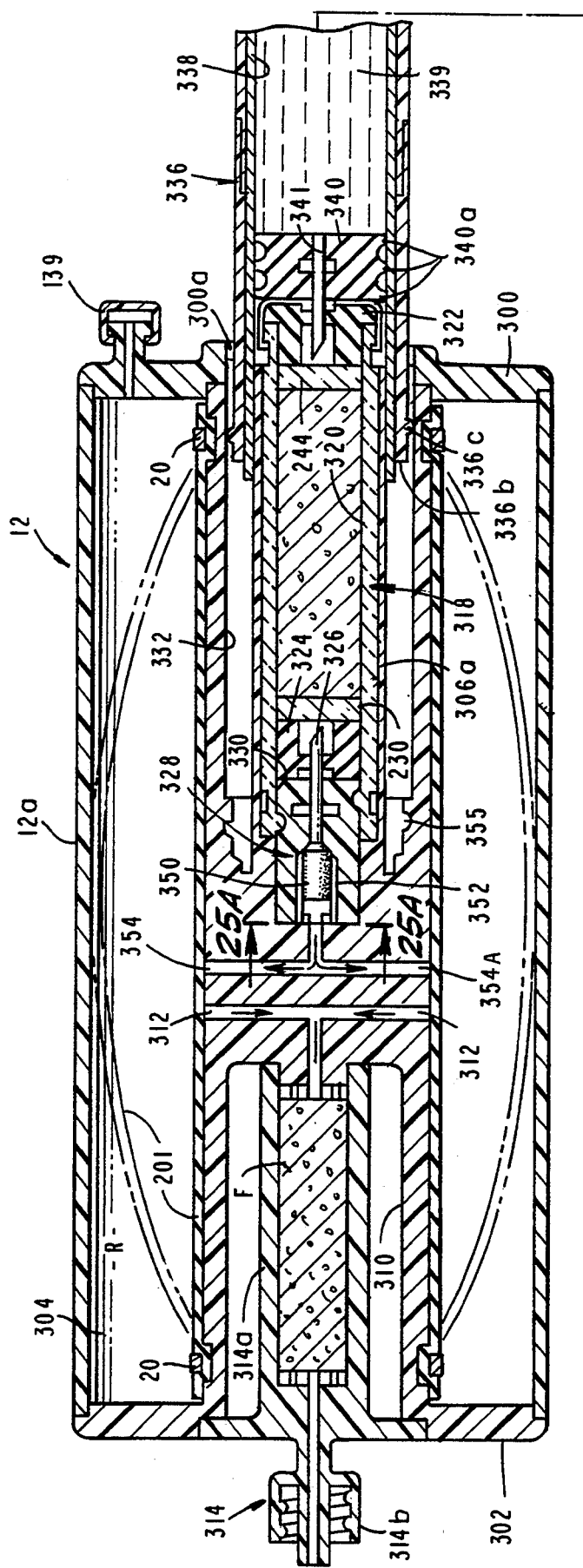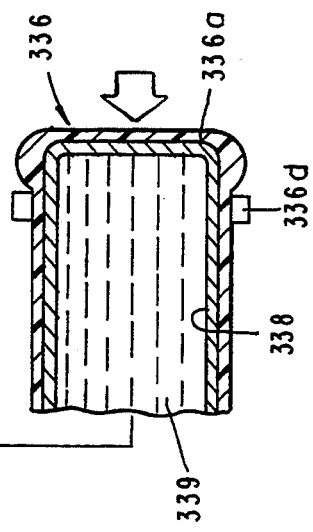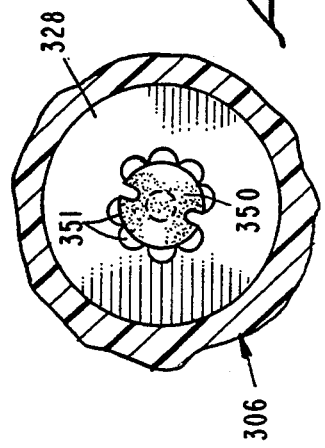
FIG. 25
FIG. 25A

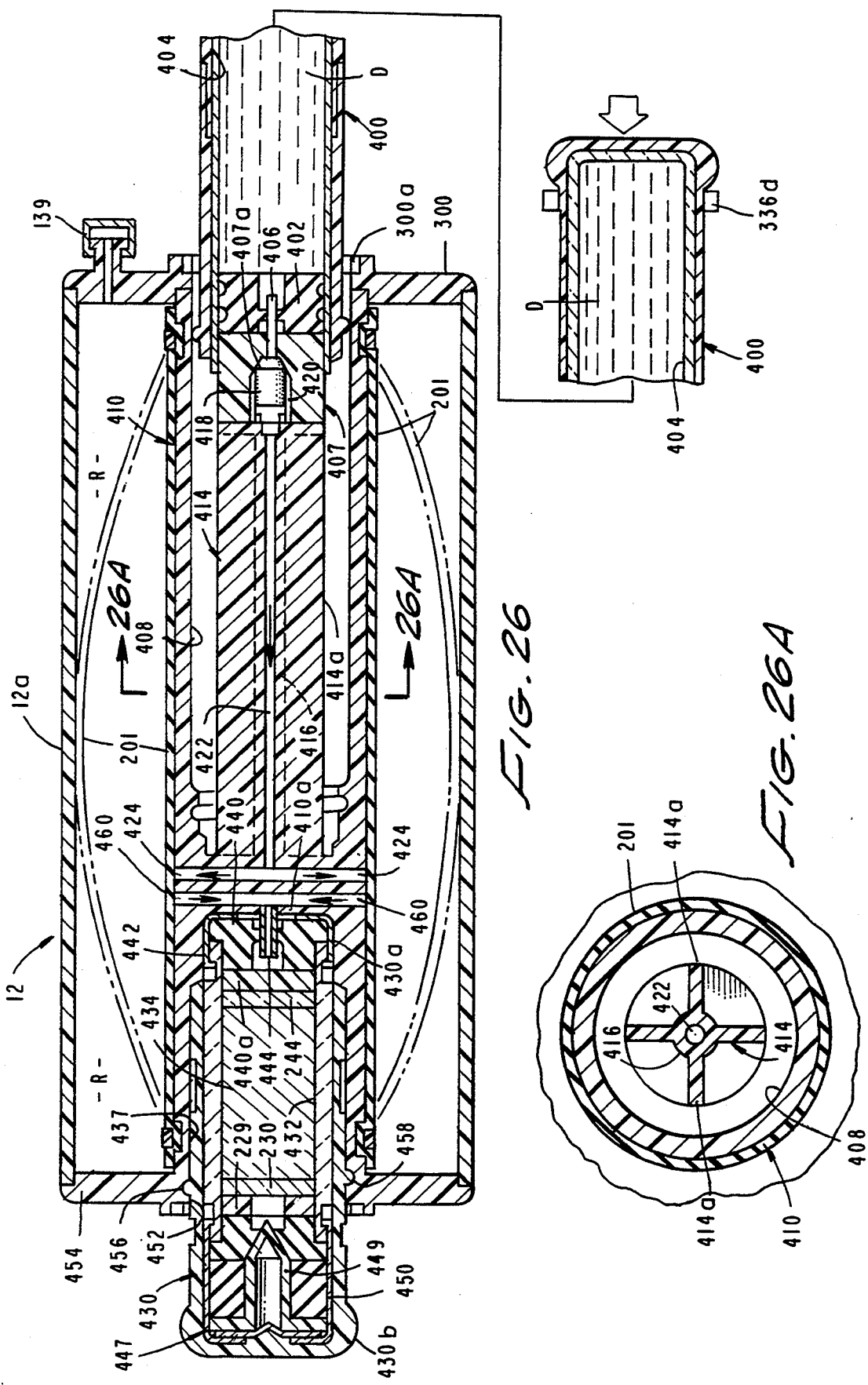

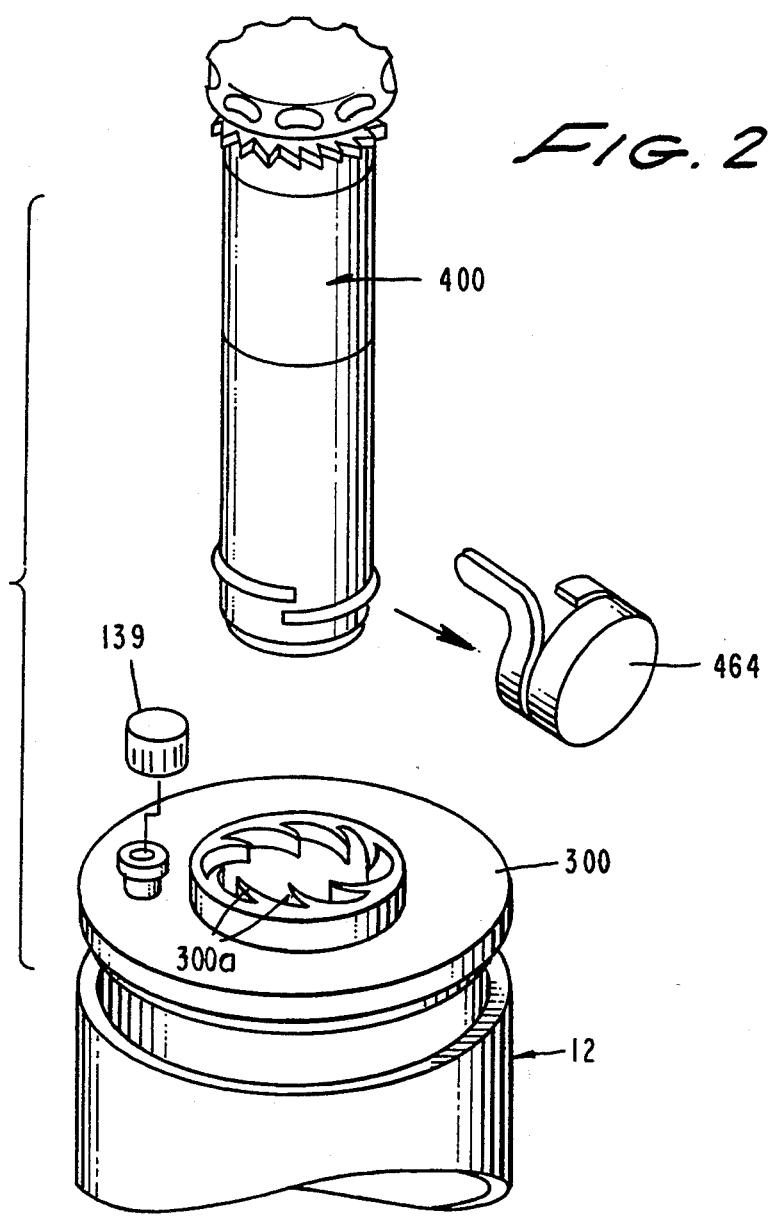
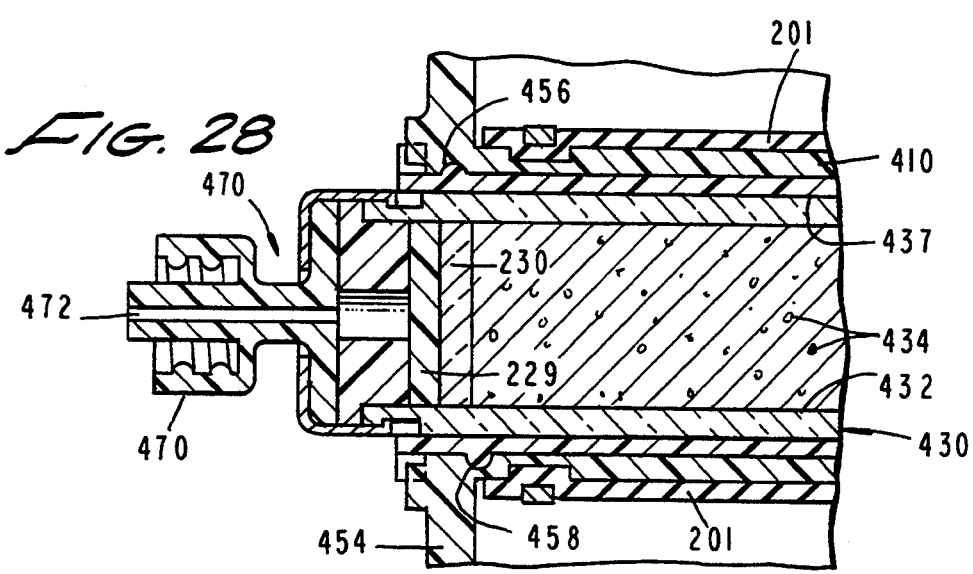

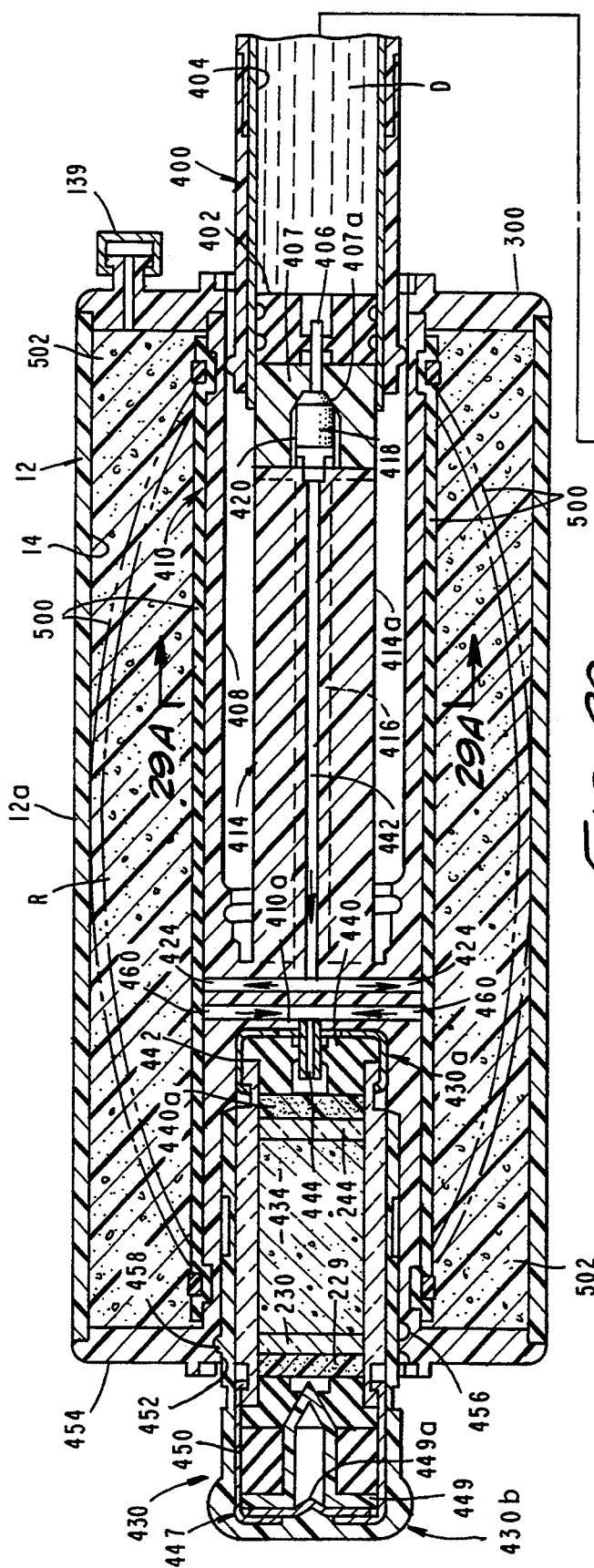
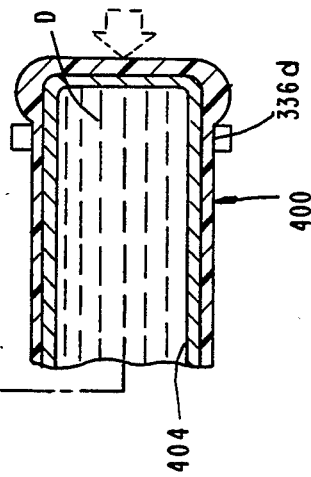
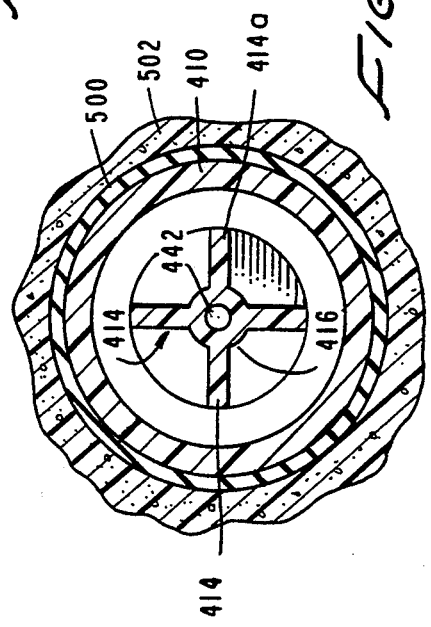
FIG. 29
FIG. 29A

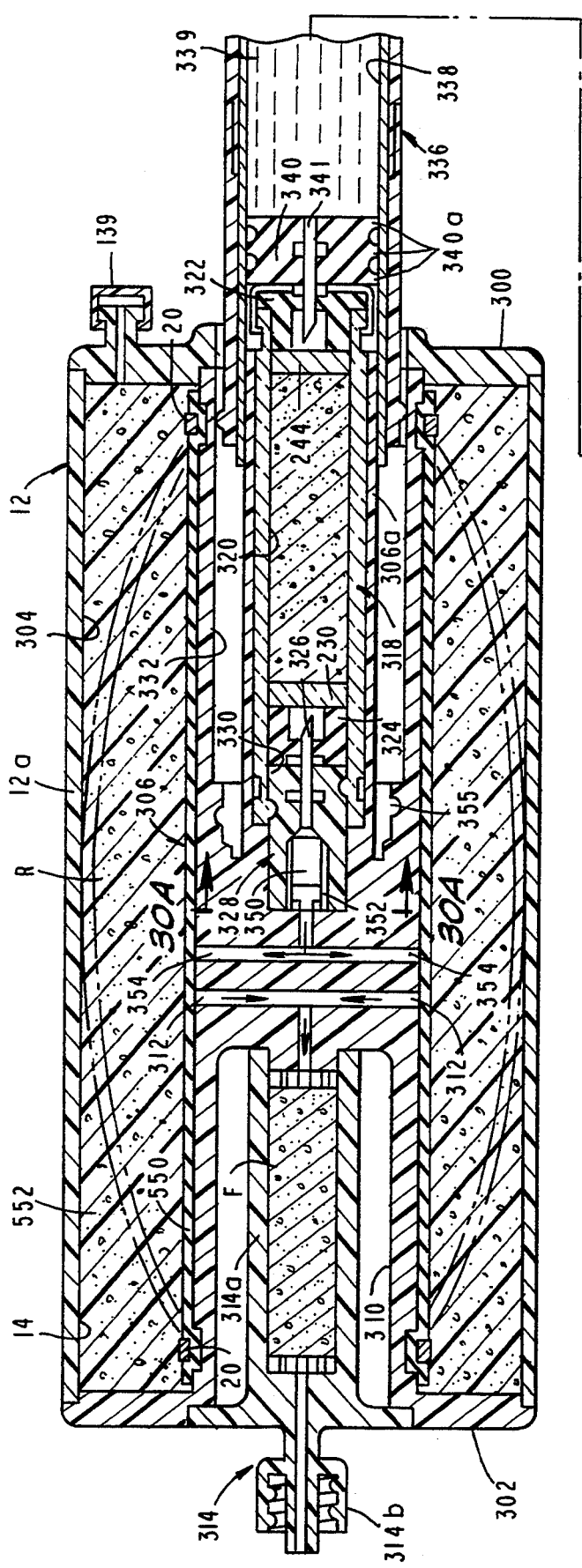
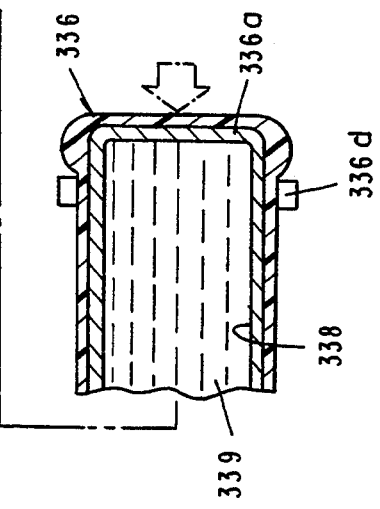
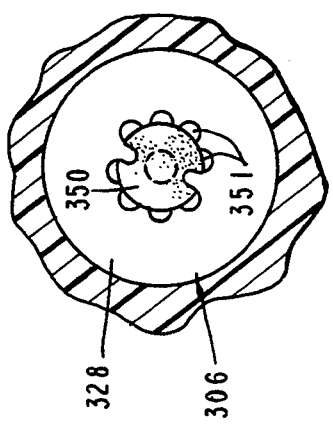
FIG. 30
FIG. 30A

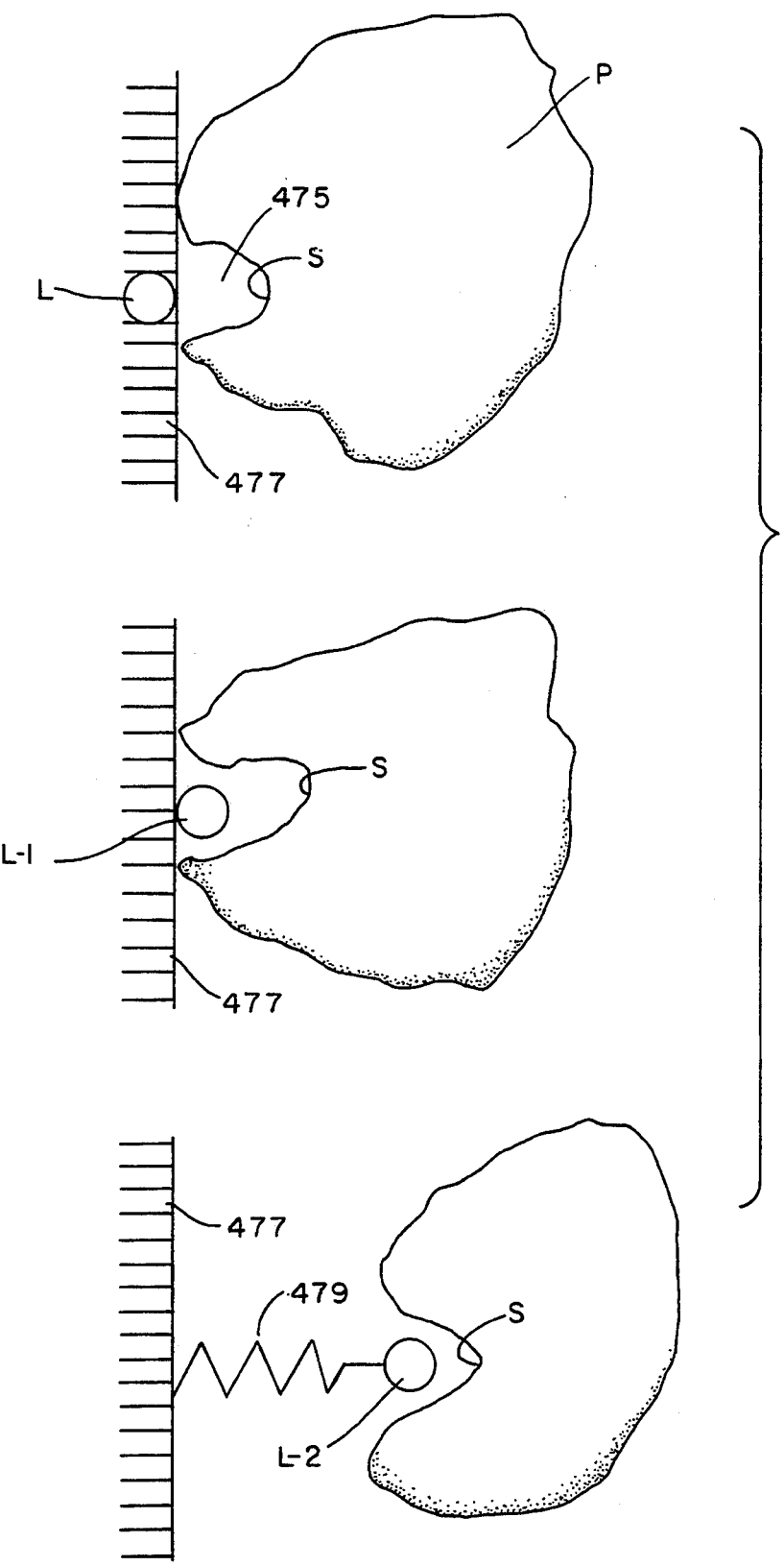

FLUID DISPENSER

BACKGROUND OF THE INVENTION

This is a Continuation-in-Part Application of co-pending U.S. application, Ser. No. 071870,521, filed on Apr. 17, 1992, now U.S. Pat. No. 5,263,940.

FIELD OF THE INVENTION

The present invention relates generally to infusion devices. More particularly, the invention concerns an elastomeric bladder type infusion device which is used for delivering a beneficial agent to a patient at a substantially constant rate. The device uniquely includes means for intermixing a first compound, such as a drug, with a second component such as a parenteral liquid prior to delivering the solution thus formed to the patient.

DISCUSSION OF THE INVENTION

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestesses the bladder in both the axial and radial directions when disposed therein, substantially filling the bladder in its unfilled state. The Hassel device also includes a one-way valve on the stress member which permits flow in the influent lumen only in the direction of the interior of the bladder.

Another type of balloon type infusion device is disclosed in U.S. Pat. No. 4,386,929 issued to Perry, et al. The Perry, et al. device has spaced apart inlet and outlet means and the bladder which is capable of expanding and contracting radially and axially upon inflation and deflation. When deflated the lumen of the bladder is substantially completely filled by lumen filling means which protect the bladder from being punctured by the hypodermic needle used to fill and inflate the bladder. The lumen filling means resists the compressive load applied during insertion of the needle and maintains the inlet and outlet means in spaced apart relationship while providing substantially no resistance to the axial expansion of the bladder. By having the lumen of the bladder filled with the lumen filling means when the bladder is deflated, before its subsequent inflation and deflation, substantially complete expulsion of the fluid contents of the bladder can be obtained.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time. In the device described in U.S. Pat. No. 3,469,578, the liquid is expelled solely by pressure induced on the liquid by the internal stresses of the distended bladder member. In the device disclosed in U.S. Pat. No. 3,468,308, the liquid is expelled by pressure control means which controls pressure applied to the exterior of the bladder member to control its rate of collapse.

In the devices described in both of the aforementioned patents, the bladder member comprises a balloon, or tube-like member which is typically distendable both lengthwise and laterally when initially pressured. Admission and discharge of liquid is of necessity, through a single neck, or outlet portion of the balloon-like bladder.

None of the prior art devices known to applicant have the unique capability of the present invention for internally mixing a first compound, such as a drug, with a second compound such as a diluent, prior to expelling the beneficial agent thus formed from the device.

SUMMARY OF THE INVENTION

It is an object of the present invention to provide an elastomeric bladder stored energy type infusion device which can be filled with a fluid such as a diluent and when during filling efficiently mixes the diluent with an additive such as a drug or other type of beneficial agent.

More particularly, it is an object of the invention to provide an infusion device of the aforementioned character which provides the opportunity to add to the diluent or other parenteral fluid being introduced into the device selected elements, chemical compounds and biologically active materials such as drugs, medicaments, biological agents, or other therapeutic agents (additives). This addition is accomplished by removably affixing the selected additives to various forms of support structures which can be placed within the path of the fluid flowing through the device. In this way, the delivery system of the invention can be safely rendered therapeutically active upon hydration of the additive with the selected parenteral fluid.

Another object of the invention is to provide an elastomeric bladder type infusion device of the class described in which make-up air can be added during the fluid delivery operation to insure that a uniform expelling of the fluid can be realized.

Another object of the invention is to provide a device of the character described in the preceding paragraphs in which a large number of additives can be selectively mixed at controlled rates with the filling fluid.

Still another object of the invention is to provide a device of the class described which includes internally disposed flow control means for precisely controlling the rate of flow of the fluid from the device.

Another object of the invention is to provide a bladder type infusion-mixing device in which the beneficial agent to be added to the filling fluid is removably affixed to supporting substrates of various materials and configuration.

Yet another object of the invention is to provide a device of the character described in the preceding paragraphs which is highly reliable inexpensive to produce in quantity, easy to use and readily disposable after use.

BRIEF DESCRIPTION OF THE DRAWINGS

FIG. 4 is a cross-sectional view very similar to FIG. 2 but showing the bladder assembly in this form of the invention in a distended position.

FIG. 5 is a cross-sectional view taken along lines 5—5 of FIG. 4.

FIG. 6 is an enlarged fragmentary, cross-sectional view taken along lines 6-6 of FIG. 4.

FIG. 7 is a cross-sectional view taken along lines 7—7 of FIG. 6.

FIG. 8 is a cross-sectional view taken along lines 8—8 of FIG. 6

FIG. 9 is an enlarged, cross-sectional view of the area designated by the numeral 9 in FIG. 4.

FIG. 10 is a generally perspective exploded view of the fluid dispensing devise of this form of the invention.

FIG. 11 is a generally perspective view of various forms of the structural support portion of the adding means of the invention for adding an additive to the fluid introduced into the storage reservoir of the device.

FIG. 15 is an enlarged, cross-sectional view of the inlet end of an alternate form of drug vial assembly of the invention.

FIG. 16 is an enlarged, fragmentary, cross-sectional view of the outlet end of the vial assembly of FIG. 15 locked in place within a fluid delivery device of slightly different construction.

FIG. 17 is an end view of the connector ring of the device of FIG. 16 which functions to lock the vial assembly in place.

FIG. 18 is a cross-sectional view taken along lines 18—18 of FIG. 17.

FIG. 19 is a side elevational, cross-sectional view of still another form of fluid delivery device of the present invention.

FIG. 20 is a greatly enlarged, cross-sectional view taken along lines 20—20 of FIG. 19 of the outlet portion of another form of the immobilized drug vial assembly in FIG. 20.

FIG. 21 is a gretly enlarged cross-sectional view taken along lines 21—21 of FIG. 19 showing the inlet portion of the vial assembly.

FIG. 22 is a side elevational, cross-sectional view of yet another form of the delivery device of the invention.

FIG. 22A is a cross-sectional view taken along lines 22A—22A of FIG. 22.

FIG. 25 is an enlarged, cross-sectional view of the device partially shown in FIG. 24.

FIG. 25A is a cross-sectional view taken along lines 25A—25A of FIG. 25.

FIG. 26 is a side elevational, cross-sectional view of yet another embodiment of the invention.

FIG. 26A is a cross-sectional view taken along lines 26A—26A of FIG. 26.

FIG. 27 is a fragmentary, exploded, generally perspective view of the filling end of the device.

FIG. 28 is an enlarged, fragmentary, cross-sectional view of the fluid outlet portion of another form of the fluid delivery device of the invention.

FIG. 29 is a side elevational, cross-sectional view of yet another embodiment of the invention which uses a different stored energy source.

FIG. 29A is a cross-sectional view taken along lines 29A—29A of FIG. 29

FIG. 30 is a side elevational, cross-sectional view of still another form of the device of the invention.

FIG. 30A is a cross-sectional view taken along lines 30A—30A of FIG. 30.

FIGS. 31A, 31B, 31C and 31D are generally diagrammatic views illustrating various means for affinity attachment of ligands, protein molecules and enzymes to the additive presentation means.

DESCRIPTION OF ONE FORM OF THE INVENTION

Figure 1:
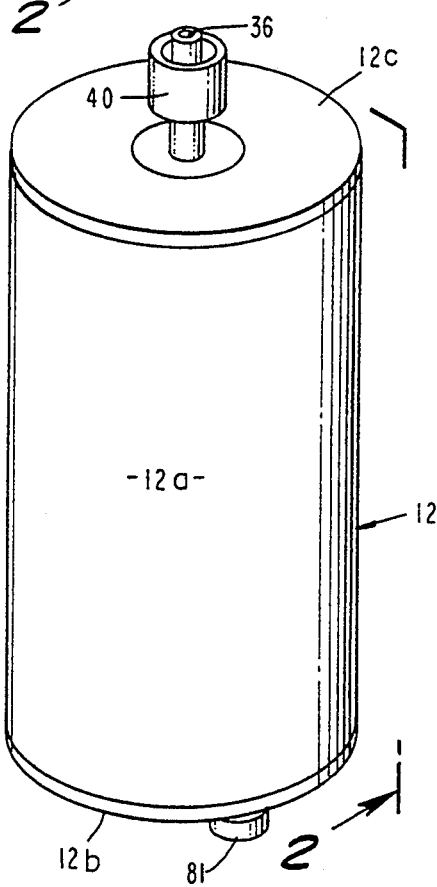
FIG. 1 is a generally perspective view of the fluid delivery device of one form of the present invention.
Figure 2:
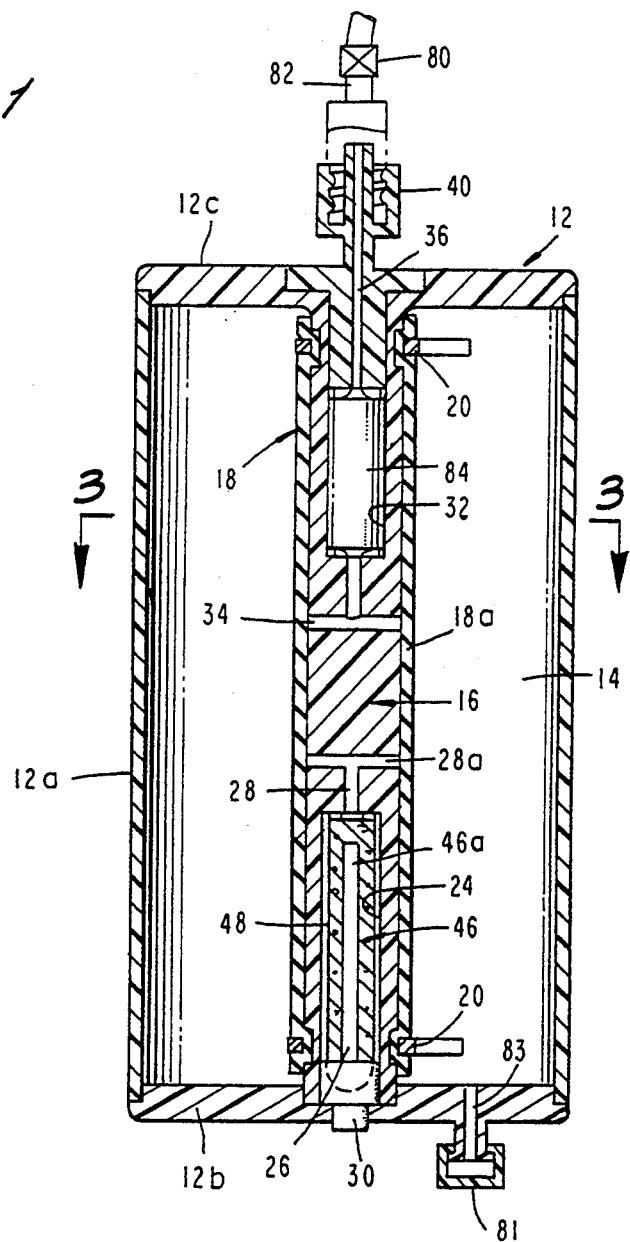
FIG. 2 is a cross-sectional view taken along lines 2—2 of FIG. 1.
Figure 3:
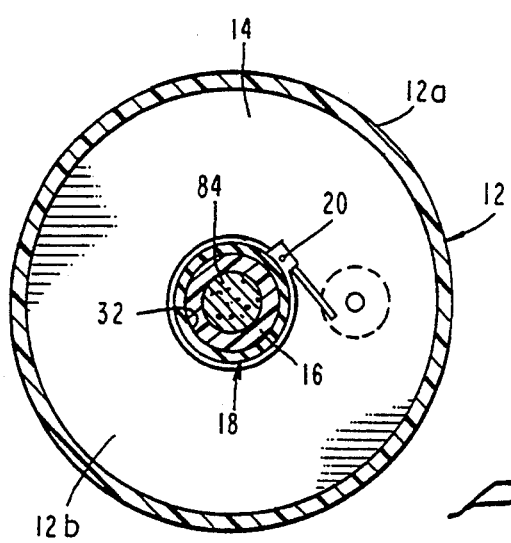
FIG. 3 is a cross-sectional view taken along lines 3—3 of FIG. 2.

Referring to the drawings and particularly to FIGS. 1, 2, and 10, the fluid dispenser of one form of the invention can be seen to comprise an elongated housing 12 having an internal chamber 14, a support 16 disposed within internal chamber 14 and extending longitudinally of the housing 12, and a generally cylindrically shaped, elongated elastomeric member 18.

Housing 12 comprises a cylindrically shaped central portion 12a and inlet and outlet end plates 12b and 12c respectively. Central section 12a and end plates 12b and 12c may be constructed of any suitable rigid plastic material such as a polycarbonate and end plates 12b and 12c can be affixed to the central section by any suitable means such as adhesive bonding or an appropriate sonic weldment. Elastomeric member 18 is securely affixed proximate its ends to support 16 by means of suitable ring clamps 20 such as self-locking plastic panduit strips.

As best seen by referring to FIG. 2, support 16 is provided with a first chamber 24 having a fluid inlet 26 and a fluid outlet 28. Fluid inlet 26 is accessible via closure means here shown as a site injection septum 30. Septum 30 can be constructed from a self-sealing, non-coring material such as silicone SEBS, which can be sealably punctured by a needled of a conventional syringe or may be provided with a slit adapted to accept a blunt cannula of a character well know to those skilled in the art. Septum 60 is receivable within one end of the chamber 24 and extends through end wall 12b of housing 12 in the manner shown in FIG. 2.

Support 16 is also provided with a second chamber 32 having an inlet fluid passageway 34 and an outlet fluid passageway 36. A fluid dispensing means shown here as a luer connector 40 is provided at the outlet end of support 16 in the manner shown in FIG. 2.

It is to be observed that elastomeric member 18 includes a central portion generally designated as 18a which overlays fluid outlet passageway 28 and fluid inlet passageway 34 of support 16.

As previously mentioned, the dispensing device of the present invention is unique in that it provides an opportunity to add to the diluent or other parenteral fluid being introduced into the device via septum 30 selected elements, chemical compounds and biologically active materials such as drugs, medicaments, biological agents and other therapeutic agents (additives).

This addition is accomplished by removably affixing selecting additives to various forms of support structures which can be placed into chamber 24 of support member 16 so that they reside within the path of the fluid flowing through inlet fluid passageway 26 and outlet passageway 28 of support member 16.

Before considering the highly important adding means of the invention a brief introductory background is perhaps helpful.

In the past it has been common practice to mix various types of separately packaged drugs with a suitable diluent immediately before they are delivered intravenously to a patent. typically the drugs are packaged separately from the diluent for various reasons. For example, many drugs do not retain their chemical and physical stability when mixed with a diluent and thus cannot be stored for any substantial period of time. Also, drugs are often packaged separately from the diluent because many firms which manufacture drugs are not engaged in the business of providing medical solutions in containers for intravenous delivery and vice versa.

Traditionally, the mixing of the drug and the diluent was accomplished by a doctor, nurse or medical professional injecting the injectable fluid into a glass vial containing the drug. After mixing the drug and the diluent, the solution thus formed is withdrawn into a syringe barrel and in some instances injected immediately into the intravenous system of a patient. More typically however, the reconstituted drug is injected from the syringes into a larger container or solution for connection to an intravenous administration set. This prior art procedure is time consuming, imprecise and generally undesirable.

The device of this latest form of the invention elegantly overcomes the drawbacks of the prior art reconstituting and delivery techniques by providing in conjunction with the basic fluid delivery device of the invention a simple and precise means for automatically mixing the desired drug with the appropriate diluent at the time the device is filled.

In the paragraphs which follow, wherein the details of this unique reconstitution process will be discussed, the following terms will have the following meanings:

Element—any of the fundamental substances that consist of atoms of only one kind and that singly or in combination constitute all matter.

Additive—the element, compound, substance, agent, biologically active material, or other material which is to be added, all or in part, to the fluid introduced into the device of the invention.

Parenteral Fluid—any solution which may be delivered to a patient other than by way of the intestines, including water, saline solutions, alkalizing solutions, dextrose solutions acidifying solutions, electrolyte solutions, reagents, solvents and like aqueous solutions.

Beneficial Aqents—any drug, medicament, pharmaceutical, medical polymer, enzyme, element, chemical compound or other material useful in the diagnosis, cure, mitigation, treatment or prevention of disease and for the maintenance of the good health of the patient.

Biologically Active Material—a substance which is biochemically, immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such biochemical compounds biologically functioning as antibodies, antigenic substances, enzymes, cofactors, inhibitors, lectins, hormones, hormone producing cells, receptors, coagulation factors, anti-fungal agents, growth enhancers, histones, peptides, vitamins, drugs, cell surface markers and toxins, among others known to those skilled in the art. Of the group of biologically active materials described, proteins are of utmost current interest because of the large molecule genetically engineered bio-pharmaceuticals as those species to be immobilized on the additive carriers hereinafter to be described. A discussion of the use of biomosaic polymers as carriers for biologically active materials is set forth in European Patent Application 0,430,517 A2.

Adding Means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a functional support, or carrier, an anchorage, a deposition site or element holder, with or without some type of intermediate matrix.

Additive Presentation Means—Any means such as a functional support or substrate for presenting the additive to the fluid flowing through the device. The functional substrate can comprise a polymer, copolymer, an inter-polymer, a ceramic, a crystal sponge, a carbon based matrix, a celullosic, glass, plastic, biomosaic polymers, azlactone-functional polymer beads, adduct beads, carboxylate-functional polymer beads, gums, gels, filaments and like carriers.

The adding means of the invention can take several different forms such as those illustrated in FIG. 11. However, in its preferred form, the adding means comprises a cylindrically shaped, microporous polymeric functional support structure 46 which is disposed within chamber 24 of the support and to which various additives, including beneficial agents such as drugs, biologically active materials, and chemical elements and compounds which can be releasably connected. These additives are carried by the structure in a manner such that, as the liquid, such as a diluent, reagent or other aqueous solvent flows through a central passageway 46a and circulates through the support assembly in the manner shown by the arrows in FIG. 6, the additives will be presented to the liquid flow and efficiently added to the liquid as it flows toward outlet passageway 28 and into the reservoir.

The additives themselves can also take various physical forms including liquid, solid, granular, powder, particle, gel, was hydrocolloid carriers, such as gum film, tablet, crystalline, emulsions, microcrystalline, microspherical, spray dried compounds and lypohilized compounds and saturants. The additives can be removably connected to immobilized on, impregnated within or supported by support means in a number of ways. The additives can be chemically or mechanically attached, affixed, or bound directly or indirectly through cooperation with an intermediate matrix. They can be captured, affixed, linked, or cross-linked, anchored to the surfaces of the support, or surface active agent, or they can be absorbed, reaction catalyzed, electrostatically encapsulated, attached by chemical modification in to the carrier surface, polymerized on or through the carrier, localized, entrapped, deposited suspended or occluded within voids, cells, tubules and intersticies formed in the support. One important method for removably affixing the additive to the functional support means includes treating the functional support means with a compound having reactive functional groups such as a azlactone functional compounds with their high binding capacity. In certain applications, the biologically active material can be bound at the surfaces of biomosaic polymers in the manner described in EPO Patent No. 0 430 517 A2. Similarly, graft copolymers can be used in the manner described in U.S. Pat No. 5,013,795 issued to Coleman, et al. In this way complexing agents, catalysts and biological materials such as enzymes or other proteins as well as biomacromolecules can be attached to the carrier.

Similarly, the additives can be immediately separated from the functional support and added to or intermixed with the liquid flowing through the device by one or more of various mechanisms, including chemical reaction, dissolution, debinding, delinking bioseparation diffusion, washing, disintegration, errosion, disassociation, desorbsion, solubilization, leeching, enzymatic cleavage, biological reaction, osmisis, separated from ring opening materials and like separation means.

Turning now to FIGS. 2 and 6, one form of adding means or additive carrier is there illustrated. This form of the adding means comprises a generally cylindrically shaped porous substrate 46.

In using the apparatus of the invention, septum or non-coring injection site 30 is penetrated by needle 47 of a syringe and a parenteral fluid, such as a sterile diluent, is introduced into inlet passageway 26 using the needle syringe. As indicated by the arrows in FIG. 6 as the diluent flows longitudinally of inlet passageway 26 it will pass through porous member 46, into flow channels 48 which surround substrate 46 (FIG. 7) and then into fluid reservoir 50 (FIG. 4 via outlet passageway 28.) Circumferentially spaced flow fins 49 direct the flow through transverse passageways 28a (FIG. 8). This diluent flow under pressure will urge bladder 18 outwardly into the position shown in FIGS. 4 and 5. As the liquid flow through porous functional support member 46, the additives presented to the liquid will be releasably separated from the functional support and added to the flow, or solubilized by the diluent, thereby activating the diluent to form the therapeutic solution to be dispenses to the patient.

The liquid, such as parenteral fluid, which is introduced into passageway 26 can include, by way of example, a reagent, a sterile diluent, various electrolytes, aqueous solutions or reagents such as aqueous solutions of dextrose, saline solutions, alkalinizing solutions, acidifying solutions, polyonic solutions and any other liquids that can serve as a vehicle for the administration of therapeutic or beneficial agents which are desirable to administer to the patient by infusion.

Turning now to FIG. 11 various other forms of adding means or additive assemblies are there illustrated. For example, numeral 54 identifies an assembly comprising a plurality of annular wafers 56 each of which is coated with the selected additive. The wafers are stacked in the manner shown in the drawing to provide a multiplicity of exposed surfaces and alternatively spaced reaction sites which are exposed to the diluent as it flows through chamber 24. Numeral 58 designates a porous substrate with interconnecting voids, such as a porous ceramic with various coatings containing one or more additives deposited within the voids. The selected additives such as elements, chemical compounds or drugs are contained within the deposited material and are deposited, or immobilized thereon by techniques well known to those skilled in the art. The additives contained within the voids are, of course, presented or exposed and then introduced into the sterile diluent as the diluent flows along the passageway 26.

Another form of additive assembly designated in FIG. 11 by the numeral 60 comprises tubular member having a multiplicity of internal, alternate sized pores which are plugged with selected additives such as chemical compounds and beneficial agents, or medicaments.

Another slightly more complex additive assembly is identified by the numeral 62. This assembly is made up of a plurality of spaced apart, porous disk shaped wafers 62a, 62b, 62c and 62d each wafer being of the same or different construction and porosity and each having a multiplicity of reactive sites presenting to the liquid flow specially selected individual species of additives such as beneficial agents, elements or compounds so that multiple reactivities and selectivities can be achieved. With this construction, a wide variety of liquid flow rates, and complex sequential separations and priority staged substance introduced into the system reservoir can be achieved by specially designing each of the wafers having unique affinity and separation characteristics that cooperate to make up the function structural support.

The numeral 64 of FIG. 11 identifies yet another form of the additive means of the invention. In this form of the invention, a generally cylindrically shaped functional support means is formed from a multiplicity of microporous polymers 64a presenting a multiplicity of reactive sites.

Still another form of the additive assembly is identified by FIG. 11 by the numeral 66. This assembly comprises a cylindrical, porous plug like member made up of a multiplicity of fused together microspheres 66a each of which is coated with a separation of reactive coating upon which is deposited an additive such as a biologically active material or other beneficial agent.

The additive assembly designated in FIG. 11 by the numeral 68 is made up of a high porosity, semi-synthetic celullosics 68a formed into a generally cylindrical shape and having interconnecting intestial surfaces and voids or functional support means and is similar in size and configuration to activating assembly 423.

Additive assembly 70 comprises a cylindrically shaped porous structure which is provided with pores of varying sizes only some of which are coated, plugged or impregnated with selected additives and as necessary functions, intermediate materials.

The additive assembly 72 of FIG. 11 comprises a cylindrically shaped structure made up of a plurality of interconnected bundles 72a the exposed surfaces of which carry the selected additive which has been removably interconnected thereto as a coating, vapor deposition or other chemical attachment.

Another form of adding means is identified in FIG. 11 by the numeral 74. Here the adding means is provided as a cylindrical structure formed form a plurality of coating, cladding, emulsion or deposition layers 74a or laminated around a porous core.

Finally, the functional support member identified in FIG. 11 by the numeral 76 exemplifies yet another form of adding means of the invention. This member, which is also of a generally cylindrically shaped configuration is constructed from a porous ceramic material into which selective additives and intermediate matrix compounds have been removably affixed.

Assemblies 54 through 76 which may be soluble or insoluble are intended to merely exemplify, not to limit, the wide variety of materials, constructions and techniques for affinity and separation that can be used to introduce the desired additives into the liquid flow introduced into the inlet flow passageway 26 of the device.

After the diluent or other parenteral fluid is introduced into the device and mixed with the additive, the solution has formed closure means such as a valve or clamp 80 provided on infusion line 82 is opened (FIG. 2). When valve 80 and venting port 83 are opened, the bladder 18, within which internal stresses have been imparted by the fluid flowing into the device via passageways to its less distended initial starting position urging fluid through passageway 34. Port 83 is normally closed by a removable cap 81. The fluid, which is now the diluent mixed with the additive, will flow into chamber 32 and through flow rate control means shown here as a porous rate control filter 84. Filter 84 can be constructed from a porous ceramic or other suitable porous plastic material such as polysulfone and can be provided with the desired porosity of a manner well known to those skilled in the art.

Figure 12:
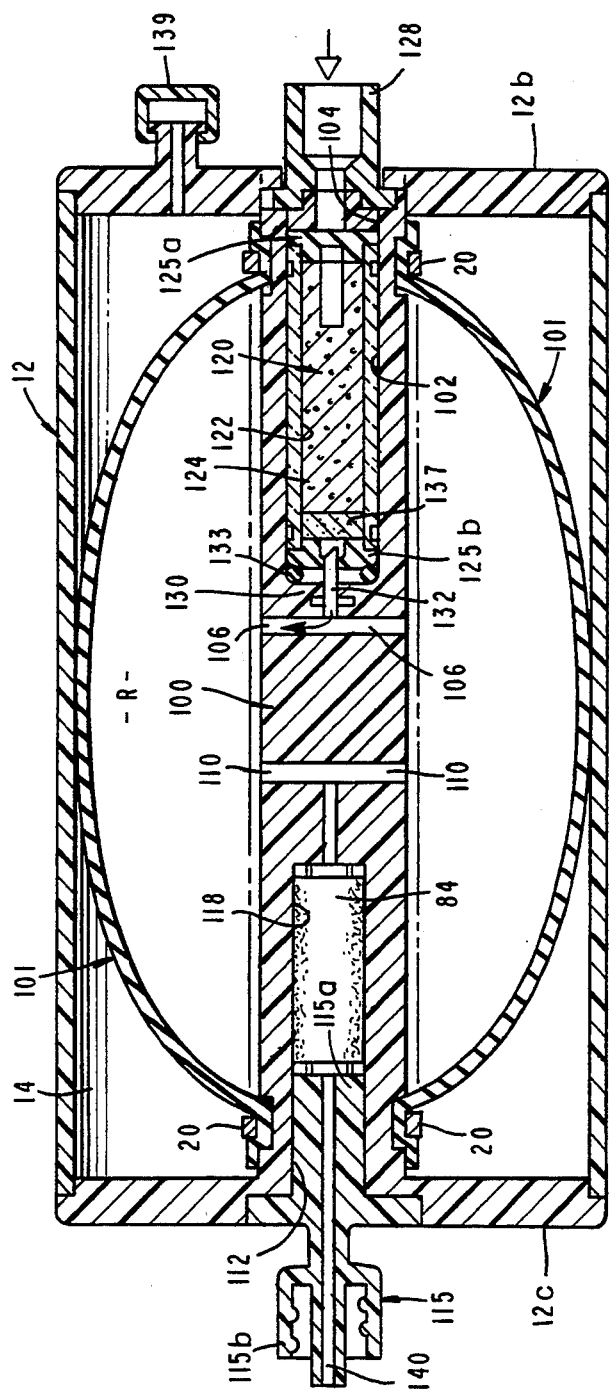
FIG. 12 is a side elevational, cross-sectional view of an alternative form of fluid delivery device of the present invention.
Figure 14:
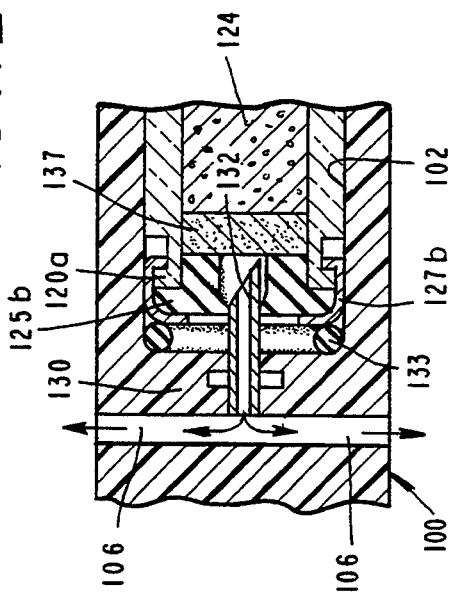
FIG. 14 is an enlarged, fragmentary, cross-sectional view of the outlet of the vial assembly showing the fluid flow path of the fluid flowing through the apparatus and outwardly toward the fluid reservoir.
Figure 13:
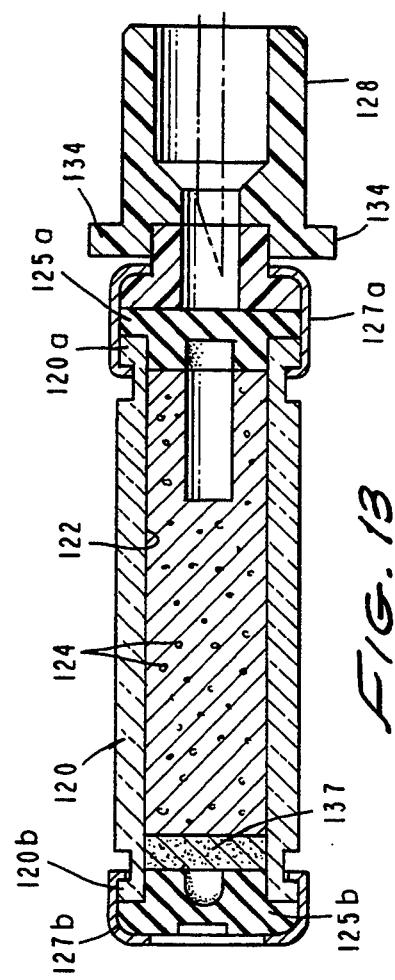
FIG. 13 is an enlarged, cross-sectional view of one form of immobilized drug vial assembly usable with the device shown in FIG. 12.

Referring now to FIGS. 12 through 14, the fluid dispenser of an alternate form of the invention is there shown. This form of the invention is similar in many respects to that shown in FIGS. 1 through 11 and like numerals are used to identify like components. This alternate embodiment comprises, an elongated housing 12 having an internal chamber 14 and a support means shown here as a support 100 disposed within internal chamber 14. Support 100 extends longitudinally of the housing 12 and supports a generally cylindrically shaped, elongated elastomeric member 101.

Housing 12 comprises a cylindrically shaped central portion 12a and inlet and outlet end plates 12b and 12c respectively. Central section 12a and end plates 12b and 12c may be constructed of any suitable rigid plastic material such as a polycarbonate and end plates 12b and 12c can be integrally formed with or affixed to the central section by any suitable means such as adhesive bonding or an appropriate sonic weldment. Elastomeric member 101 is securely affixed proximate its ends to support 100 by means of suitable ring clamps 20 such as self-locking plastic panduit strips.

Support 100 is provided with a first chamber 102 having an opening 104 and fluid outlets 106 leading to reservoir "R". Opening 104 is adapted to receive the adding means of this form of the invention for adding a selected additive to the fluid flowing toward reservoir "R".

Support 100 is also provided with a second chamber 108 having inlet fluid passageways 110 which communicate with reservoir "R". Receivable within a bore 112 formed in support 100 is a fluid dispensing means shown here as a luer connector assembly 115 which includes a body portion 115a and a luer connector 115b. Receivable within chamber 108 is filter means, shown here as filter member 84, which is of the character previously described, for filtering fluid flowing from reservoir "R" outwardly of the device. Filter member 84 can also function as a rate control means for precisely controlling the rate of fluid flow from the device.

Referring particularly to FIG. 13, the adding means here comprises a sealed cartridge 120 having an additive-containing chamber 122 for containing an additive generally designated in FIG. 13 by the numeral 124. Additive 124 can be any material of the character defined in the preceding paragraphs and, for certain applications, can be removably interconnected with a substrate or other additive presentation means of the character herein defined. Cartridge 120 is closely receivable within chamber 102 and has first and second ends 120a and 120b which are sealed by sealing means shown here as septums 125a and 125b respectively. Septums 125a and 125b are held in place by annular crimp caps 127a and 127b. Septums 125a and 125b can be constructed from a self-sealing, non-coring material such as silicone SEBS, which can be sealably punctured by a needle of a conventional syringe or they may be provided with a slit adapted to accept a blunt cannula of a character well known to those skilled in the art.

Provided at the inlet end of cartridge assembly 120 is a guide member 128 for guiding the needle of a syringe as indicated in phantom in FIG. 13.

Affixed to a transverse wall 130 of support 100 and extending into chamber 102 is a hollow needle 132. As best seen in FIG. 14, an elastomeric O ring 133 is disposed within chamber 102 proximate wall 130. When cartridge 120 is inserted into chamber 102 via opening 104, circumferentially spaced radially outwardly extending tabs 134 provided on guide member 128 (FIG. 13) are aligned with slots provided in end wall 12b (not shown). By pushing the cartridge inwardly against O ring 133, tabs 134 will clear the inside surface of wall 12b so that the cartridge can be rotated to move the tabs out of index with the receiving slots. The O ring will then urge the cartridge assembly outwardly so that the tabs engage the inner surface of wall 12b thereby locking the cartridge assembly in position within chamber 102.

As the cartridge assembly is pushed forwardly into chamber 102, needle 132 will pierce septum 125b in the manner shown in FIG. 14 thereby opening additive-containing chamber 122 to fluid communication with flow passageways 106. When fluid, such as a diluent is then introduced into chamber 102 through a syringe needle in the manner illustrated in FIG. 13, the diluent will flow into a cylindrical cavity 135 provided in additive 124 (FIG. 12), then around, about and through the additive 124, through a glass frit 137 and into the interior passageway of inlet needle 132. The fluid mixture will then flow through passageways 106 toward reservoir "R". As the mixture flows under pressure through passageways 106, it will distend member 101 and move the central portions thereof outwardly into engagement with the wall of cylindrically shaped member 12 in the manner shown in FIG. 12. Air within chamber 14 can be released to atmosphere by removing vent cap 139. This outward distention of member 101 will cause the build-up of internal stresses within the member tending to continuously return it toward its non-distended configuration. When the outlet passageway 140 of the delivery subsystem is open for fluid flow, as, for example, by opening an external valve (not shown) member 101 will function as the energy source to force the infusible mixture contained within the reservoir outwardly of the device.

Turning now to FIGS. 15 through 18, a slightly different form of the invention is there shown. The apparatus itself is virtually identical to that previously described and like numerals have been used to identify like components. The major difference in the embodiment of the invention shown in these figures resides in the manner by which the drug vial or additive assemblage is locked within the inlet chamber of the central support and the manner in which fluid is introduced into the device to charge the reservoir. Considering first, the filling aspect, rather than using a filling syringe, a luer connector assembly 141 is here provided. As best seen in FIG. 15, the cartridge assembly 142 of the adding means here includes a check valve 144 which is contained within a chamber 145 provided in the inlet end of cartridge assembly 142 (see also FIGS. 7 and 8). Luer connector assembly 141 is fixedly receivable over a boss 146 provided on the connector assembly. Boss 146 includes a fluid inlet passageway 147 which is normally closed by check valve 144. However, when the luer connector is emplaced over boss 146 and fluid pressure is applied to the check valve, it will move to the left into an open position permitting fluid flow into cylindrical chamber 135 of the adding means.

To irreversably lock the cartridge assembly in position within the inlet chamber of the support member, identified in FIG. 16 by the numeral 150, there is provided an annular locking ring 152 which is disposed within an annular groove 153 provided in the support member. As best seen in FIGS. 17 and 18, ring 152 includes a resiliently deformable, radially inwardly extending flange 155. With this construction, as the cartridge assembly 142 is inserted into the inlet chamber of the support 150, a needle 158 will pierce septum 125b in the manner shown in FIG. 16 and flange 155 will deform and then snap back into a locking position within an annular groove 159 provided in the housing 142.

Referring now to FIGS. 19 through 21, still another form of the invention is there shown. This form of the invention is similar in many respects to that shown in FIG. 12 and like numerals are used to identify like components. However, in this latest form of the invention, the adding means is disposed proximate the outlet of the device rather than proximate the inlet. This alternate embodiment comprises an elongated housing 12 having an internal chamber 14, a support 200 disposed within internal chamber 14 and extending longitudinally of the housing 12, and a generally cylindrically shaped, elongated elastomeric member 201. Support 200 is formed in two portions 200a and 200b which are connected in the manner shown in FIG. 19.

As before, housing 12 comprises a cylindrically shaped central portion 12a and inlet and outlet end plates 12b and 12c respectively. Central section 12a and end plates 12b and 12c may be constructed of any suitable rigid plastic material such as a polycarbonate and end plates 12b and 12c can be affixed to the central section by any suitable means. Elastomeric member 201 is securely affixed proximate its ends to support 200 by means of suitable ring clamps 20 such as self-locking plastic panduit strips.

Support portion 200a is provided with a first chamber 202 having an opening 204 and fluid outlets 206 leading to reservoir "R". Opening 204 is adapted to receive first valve means for controlling the flow of fluid through passageways 206. This first valve means here comprises an elongated body 207 having a central passageway 208 adapted to communicate with passageways 206. Disposed adjacent body 207 is a valve housing 209 having a valve seat 210. Housing 209 has a central chamber 212 within which a valve member 213 is movable from a first closed position to a second open position. Chamber 212 is in communication both with passageway 208 and with an inlet passageway 214 which terminates at its outboard end in a luer fitting 215.

Support portion 200b is provided with a second chamber 216 which is adapted to receive the adding means of this embodiment of the invention for adding a selected additive to the fluid flowing from reservoir "R". Referring also to FIGS. 20 and 21, the adding means here comprises a sealed cartridge 220 having an additive-containing chamber 222 for containing an additive generally designated in FIG. 20 by the numeral 224. Additive 224 can be any material of the character defined in the preceding paragraphs and, for certain applications, can be removably interconnected with a substrate or other additive presentation means of the character herein defined. Cartridge 220 is closely receivable within chamber 216 and has first and second ends 220a and 220b. End 220a is externally threaded and is threadably receivable within an internally threaded opening 217 provided in support portion 200b (FIG. 20). End 220b is initially closed by a closure assembly 221 which includes a pierceable sleeve 222a that is pierceable by a delivery spike of a character well known in the art. Closure assembly 221 is held in place by an annular crimp cap 227. Sleeve 222a is supported by an elastomeric support member 225 and can be constructed from a pierceable material such as rubber, which can be punctured by a conventional delivery spike to open a fluid flow path with a fluid passageway 228 formed in a porous spacer plug 229. Passageway 228 communicates with chamber 222 of the adding means via a glass frit 230 (FIG. 20). Porous frit 230, can in some instances, also function as a rate control means for controlling the rate of fluid flow outwardly of the device.

As best seen in FIG. 21, support portion 200a is provided with a chamber 232 which houses a valve member 234. Valve member 234 includes a neck portion 234a which is engageable by an operating member 236 provided at the end-board end of cartridge 220 so that, as the cartridge is threadably mated with support portion 200b, valve member 234 will be moved from a closed position to an open position shown in FIG. 21. With the valve in the open position, fluid will be permitted to flow from reservoir "R" into passageways 206, past valve seat 240 and into chamber 222 via a passageway 242 and a glass frit 244. As the fluid enters chamber 222, it will flow around, about and through the additive support in a manner to controllably intermix the additive carried by the additive support with the fluid.

In using the apparatus of this latest form of the invention, a source of fluid under pressure is connected to luer fitting 215. The fluid under pressure will urge valve member 213 to move to the left permitting fluid to flow into passageway 208, through passageways 206 and into reservoir "R". With the reservoir charged, cartridge 220 is introduced into chamber 216 and threadably mated with support portion 200b. This causes valve member 234 to move to the right permitting fluid flow into the adding means via passageways 242. A suitable delivery spike assembly is used to pierce member 222a permitting fluid to flow from the reservoir through the adding means and outwardly of the device via the delivery spike assembly.

Figure 23:
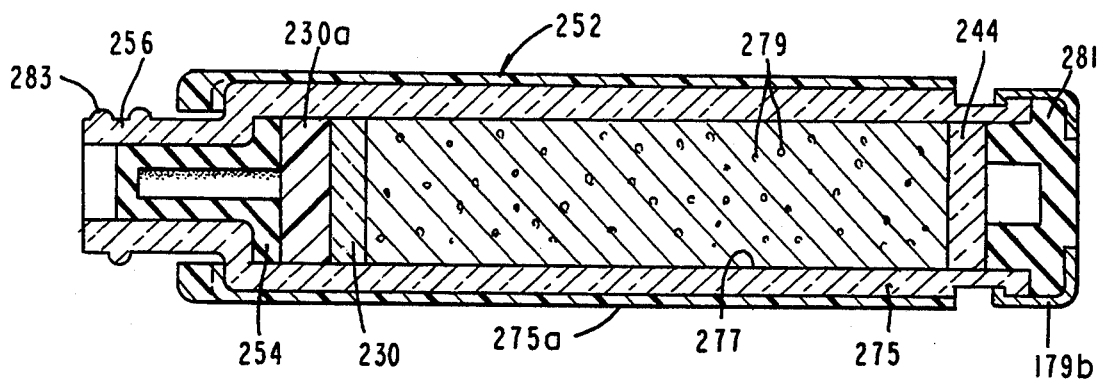
FIG. 23 is an enlarged side elevational, cross-sectional view of the drug vial assembly shown in FIG. 22.

Turning now to FIGS. 22, 22A and 23, a slightly different form of the invention is there shown. The apparatus itself is quite similar to that shown in FIG. 12 and like numerals have been used to identify like components. The major difference in the embodiment of the invention shown in FIGS. 22 and 23 resides in the manner by which the drug vial or additive assemblage is introduced within the inlet chamber of the central support. As best seen in FIG. 23, the cartridge assembly 252 of the adding means here includes a septum 254 which is contained within the threaded neck portion 256 of cartridge assembly 252. Neck portion 256 is threadably receivable within a threaded opening 257 provided in the support body 258 (FIG. 22). Body 258 includes a fluid passageway 260 which is defined by the central passageway of a needle 262 which is carried by body 258 in a manner so as to pierce septum 254 when cartridge assembly 252 is threadably connected to support body 258 in the manner shown in FIG. 22. Connected to body 258 is an inlet section 259 which forms a part of inlet end plate 259a.

To lock the cartridge assembly in position within the inlet chamber 258a of support member 258, member 258 is with a plurality of circumferentially spaced, yieldably deformable locking tabs 263. As best seen in FIG. 22A, tabs 263 engage locking teeth 252a provided on the cartridge assemly 252 in a manner to resist rotation of the cartridge assembly in a counterclockwise, loosening direction.

As in the previously described embodiment of the invention, housing 12 comprises a cylindrically shaped central portion 12a and inlet and outlet end plates 259a and 12c respectively. Elastomeric member 201 is securely affixed proximate its ends to end plate inlet section 259 and to support 258 by means of suitable ring clamps 20 such as self-locking plastic panduit strips.

Support 258 is provided with fluid outlets 106 which communicate with needle 262 and with reservoir "R". Support 258 is also provided with a second chamber 108 having inlet fluid passageways 110 which communicate with reservoir "R". Receivable within bore 112 is a fluid dispensing means shown here as a luer connector assembly 115 which includes a body portion 115a and a luer connector 115b. Body portion 115a is provided with a central fluid passageway 115c. Also receivable within chamber 108 is filter means, shown here as a filter member "F", for filtering fluid flowing from reservoir "R" outwardly of the device. As before, filter member "F" can also function as a rate control means.

As was the case in the earlier described embodiments, the adding means shown in FIG. 22 here comprises a glass vial 275 having an additive-containing chamber 277 for containing an additive generally designated in FIG. 23 by the numeral 279. Additive 279 is disposed between porous glass frits 244 and 230. Distal to frit 230 is a porous distribution plub 230a which can be any material of the character defined in the preceding paragraphs and, for certain applications, can be removably interconnected with a substrate or other additive presentation means of the character herein defined. Vial 275 is contained within a plastic overwrap 275a which includes a tear away cover (not shown) that can be removed at time of use to expose threads 283 provided on neck 256.

In using the apparatus shown in FIG. 22, fluid such as a diluent, can be introduced into vial 275 via a syringe assembly (not shown) having a hollow needle adapted to pierce a septum 281 which is provided in the inlet end of the vial. Fluid flowing into the vial will intermix with the additive in the manner previously described and the mixture will then flow toward the reservoir "R" via needle 262 and passageways 106 causing elastomeric member 201 to distend outwardly in the manner shown in FIG. 22. Dispensing of the fluid mixture is accomplished in the manner previously described.

Figure 24:
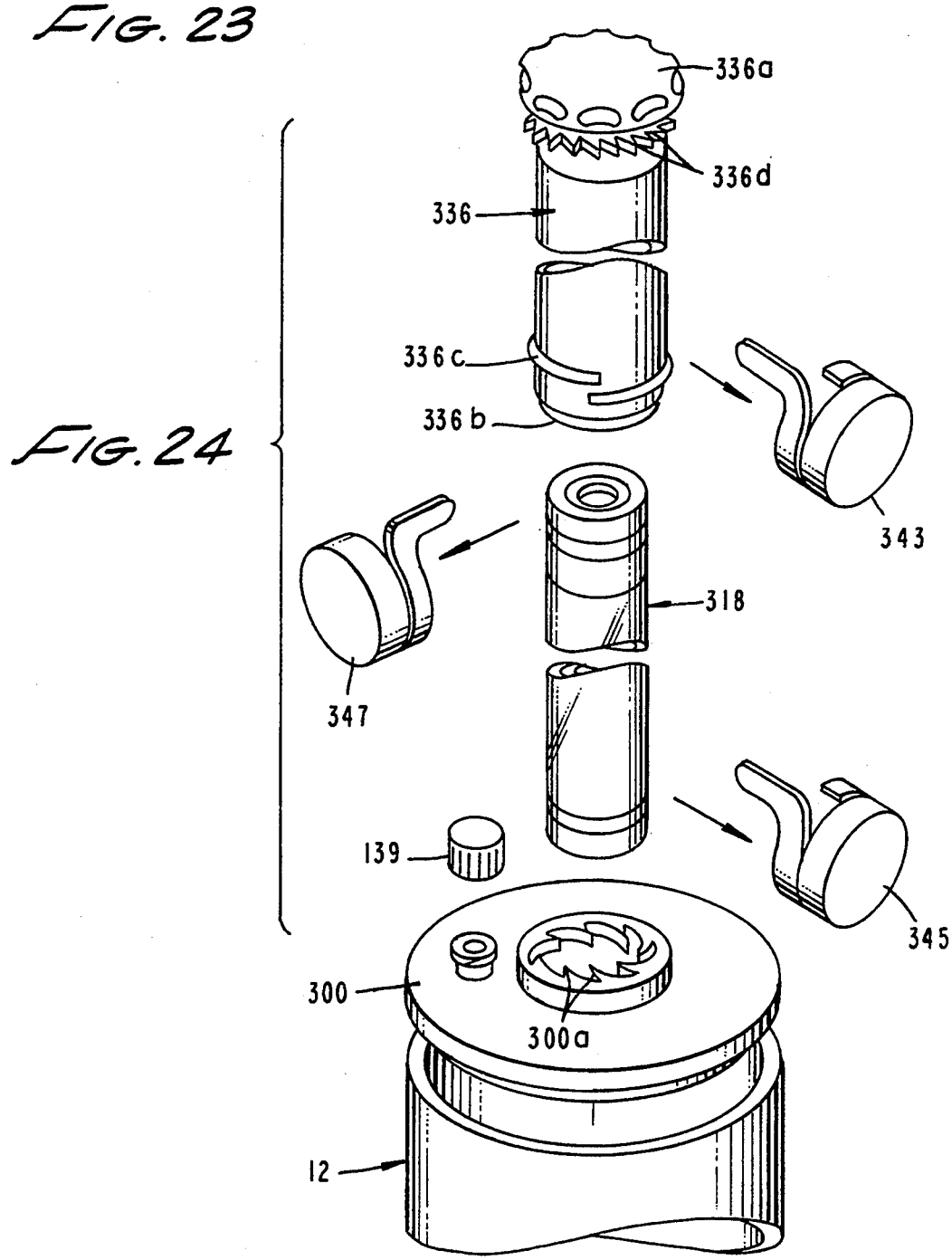
FIG. 24 is a generally perspective exploded view of another embodiment of the invention which includes a novel filling assembly for use with still another form of drug vial assembly.

Referring to FIGS. 24 through 25A, a somewhat different form of the invention is there shown. While the apparatus is quite similar to that previously described and like numerals have been used to identify like components, the drug vial or additive assemblage is first secured within the inlet chamber of the central support of the device and fluid is then introduced into the device to charge the reservoir by means of a separate cooperating diluent vial.

As best seen in FIG. 25, once again the housing 12 comprises a cylindrically shaped central portion 12a to which end plates 300 and 302 are connected to define an internal chamber 304. Support means in the form of a support 306 is disposed within chamber 304 and extends longitudinally thereof. As before an elastomeric member 201 is connected to support 306 by suitable clamps 20. Support 306 is provided with an outlet chamber 310 and includes fluid passageways 312 leading to reservoir "R". Receivable within chamber 310 is a fluid dispensing means, shown here as a luer connector assembly 314, which includes a body portion 314a and a luer connector 314b. Receivable within body portion 314a is a filter means "F" for filtering fluid flowing from reservoir "R" toward the dispensing means.

The cartridge assembly 318 of the adding means of this form of the invention shown in FIG. 25 includes a chamber 320 which is sealed at either end by septums 322 and 324. As before, the septums can be constructed from a self-sealing, non-coring material such as silicone SEBS which can be sealably punctured by a hollow needle such as needle 326 which is mounted in a valve housing 328 carried within a chamber 330 provided in support 306. It is to be noted that the cartridge assembly is internally threaded while the valve housing 328 is provided with a mating thread. With this construction, as the cartridge assembly 318 is inserted into the inlet chamber 332 of support 306 and is moved into a seated position, needle 326 will pierce septum 324 in the manner shown in FIG. 25. This opens fluid communication between the internal chamber 320 of the cartridge assembly and the reservoir "R".

Receivable over tubular wall 306a which circumscribes cartridge assembly 318 is a diluent container 336. Container 336, which may be a glass vial, includes a fluid reservoir 338 for containing the liquid component or parenteral fluid 339 as defined herein. During the charging and mixing step, fluid container 336 is telescopically receivable over wall 306a in the manner shown in FIG. 25. In the present form of the invention, reservoir 338 of the container is closed by a piston 340 which is telescopically movable within fluid reservoir 338 from a first position shown in FIG. 25 to a second position wherein the piston is disposed proximate the closed end 336a of the container. Piston 340 is provided with a plurality of circumferentially extending sealing beads 340a which sealably engage the inner walls of container 336 as the piston moves inwardly of reservoir 338. Affixed to piston 340 is an outwardly protruding hollow needle 341, the purpose of which will presently be discussed. A tear-away-type removable cover 343 encapsulates the forward face of piston 340 and sealably closes end 336b of the fluid container. After container 336 has been filled with a suitable first component, such as a parenteral fluid 339, piston 340 is inserted into the open end of the container and sealing cap 343 is emplaced over the assemblage thus formed so as to maintain the first component, such as a diluent, in a sterile, sealed condition until time of use.

In using the apparatus of this latest form of the invention, caps 345 and 347 which are provided at either end of the cartridge assembly are first removed in the manner shown in FIG. 24. Vent cap 139 is also removed. The cartridge assembly 318 is then inserted into the open end of chamber 332 and is threadably mated with valve member 328. As the cartridge subassembly mates with member 328, hollow needle 326 will penetrate septum 324 of the cartridge assembly in the manner shown in FIG. 25.

With the cartridge assembly positioned within chamber 332 in the manner shown in FIG. 25, tear-away cap 343 of the fluid container assembly 336 is removed and the container is emplaced over tubular wall 306a which surrounds the cartridge assembly. As the container assembly is urged to the left as viewed in FIG. 25, needle 341 will pierce septum 322 of the cartridge assembly opening a fluid path between reservoir 338 and the interior chamber 320 of the cartridge assembly. Continued inward telescopic movement of the fluid container will cause piston 340 to move inwardly of the fluid container forcing the diluent 339 through hollow needle 341, through porous glass frit 244 and then around, about and through the additive disposed within chamber 320. The fluid mixture thus formed will flow through the inboard glass frit and into hollow needle 326 causing a valve member 350, which is carried within a cavity 352 provided in member 328, to move to the left or open position. This, in turn, will permit the fluid mixture to flow into circumferentially spaced fluid passageways 351 provided in member 328 (FIG. 25A) and then into passageways 354 formed in support 306. The fluid flowing through passageways 354 will pressurally engage elastomeric member 201 causing it to distend outwardly in the manner shown by the phantom lines in FIG. 25.

When piston 340 of the diluent container reaches the end of reservoir 338, a thread 336c, which is provided on the outer wall of container 336, will move into threaded engagement with an internal thread 355 provided within chamber 332 of support 306. Continued rotation of fluid container 336 will then cause tabs 336d (FIG. 24) to lockably engage teeth 300a provided on end plate 300 thereby preventing removal of the container assembly from the dispensing device.

During dispensing of the fluid mixture from the device, the fluid mixture will be forced through passageways 312 by the distended member 201 which moves from the first outwardly distended position to the second position wherein it is disposed proximate the support means. The mixture will then flow through filter "F" and outwardly of the device via the luer connector assembly 314.

Turning now to FIGS. 26 through 28, still a slightly different form of the invention is there shown. The apparatus is again quite similar to that just described and like numerals have been used to identify like components. The major difference between the embodiment of the invention shown in these figures and that just described resides in the fact that the adding means is disposed in the outlet portion of the device rather than in the inlet portion. The diluent container 400 is of similar construction to diluent container 336, but the piston 402 which moves within the reservoir 404 of the container is pierceable by a blunt end cannula 406 which is molded into a valve housing 407 disposed within the inlet chamber 408 of the support means. The reservior "R" of the device is filled by urging container 400 telescopically inwardly of chamber 408 causing cannula 406 to pierce piston 402 and causing the piston to move longitudinally of container reservoir 404. As container 400 moves inwardly of chamber 408, it is guided by guide means shown here as a cross-like guide member 414 which is carried by a longitudinally extending hollow column 416 and which includes four radially outwardly extending legs 414a the extremities of which guidingly engage the interior wall of container reservoir 404.

Fluid, such as diluent "D" flowing from reservoir 404 through cannula 406 will cause a valve member 418, which is carried within a chamber 420 provided in housing 407, to move to the left and away from valve seat 407a permitting fluid to flow toward reservoir "R" via central passageway 422 provided in column 416. The fluid flowing through passageway 422 will flow under pressure through radially outwardly extending passageways 424 provided in support 410 and, as before, will cause elastomeric member 201 to distend outwardly in the manner shown in FIG. 26.

As best seen in FIG. 26, in this latest form of the invention, the adding means is disposed proximate the outlet of the device and comprises a sealed cartridge assembly 430 having an additive-containing chamber 432 for containing an additive generally designated in FIG. 26 by the numeral 434. Once again additive 434 can be any material of the character defined in the preceding paragraphs. Forming an important part of this embodiment of the invention wherein the adding means is disposed in the outlet of the device, is the unique feature for commonality of use with selected assemblies that contain both flow rate control means and an additive having an extended release rate. By appropriate selection of assembly, this feature allows for individual control of the rate of dosing of the beneficial agent into the elution diluent independent of the rate of flow of the elution diluent.

The manual facility to individually control through proper assembly selection, the delivery of both drug dosing rate and diluent dispensing rate, over a given time period, is a desirable feature. In practice, alternate vial cartridges 430 (FIG. 26) can be provided which control fluid flow rate at a given level. This capacity can insure delivery of a required dosage within a therapeutically acceptable time period over a broad range of fluid flow rates.

Additionally, the control of dosage rates and diluent flow rates can help prevent over-concentration of an administered drug which can result in patient local or systemic toxicity. More specifically, by placing the adding means in the outlet portion of the device, a selected one of any number of different types of adding means or cartridge assemblies can be selected for use with the device to affect the desire treatment protocol. By also selecting a cartridge assembly having appropriate rate control porous frits, the desired delivery rate of a selected beneficial agent can be achieved. Additionally, cartridges containing beneficial agents having extended release dosing rates over time can be selected for use with the device. Stated another way, through selection of an appropriate adding means having the desired desorption affinity release characteristics over time, combine with alternate flow rate control formats permits a wide range of delivery protocols to be realized.

Cartridge 430 is closely receivable within an outlet chamber 437 provided in support 410 and has first and second ends 430a and 430b. End 430a is sealably closed by a septum 440 which is held in place by a crimp cap 442 which exposes septum 440. Septum 440 is pierceable by a hollow needle 444 which is mounted on a transverse wall 410a of support 410. End 430b of the cartridge is closed by a closure assembly 447 which includes a pierceable sleeve 449 that is pierceable by a delivery spike of a character well known in the art. Closure assembly 447 is held in place by an annular crimp cap 450 which exposes sleeve 449. Sleeve 449 can be constructed from a pierceable material such as rubber, which can be punctured by a conventional delivery spike to open a fluid flow path which communicates with chamber 432 of the adding means via a glass frit 230 and porous distribution plug 229.

In this latest form of the invention, cartridge assembly 430 is inserted into outlet chamber 437 through an opening 452 provided in end wall 454 and a thread 456, provided on a cartridge overpackage 430a, is mated with a thread 458 provided on support 410. As the cartridge assembly is threadably mated with the support, needle 444 will penetrate septum 440 establishing fluid communication between chamber 432 of the cartridge assembly and reservoir "R" via hollow needle 444 and passageways 460 provided in support 410.

After container 400 has been filled with a suitable first component such as a diluent "D", piston 402 is inserted into the open end of the container and sealing cap 464 (FIG. 27) is emplaced over the assemblage thus formed so as to maintain the first component in a sterile, sealed condition until time of use.

With the cartridge assembly positioned within chamber 437 in the manner shown in FIG. 26, tear-away cap 464 of the fluid container assembly 400 is removed and the container is inserted into the opening provided in end wall 300 of the housing 12. As the container assembly is urged to the left as viewed in FIG. 26, needle 406 will pierce plug 402 opening a fluid path between reservoir 404 and check valve chamber 420 of valve housing 407. Continued inward telescopic movement of the fluid container will cause the check valve to open permitting the diluent to flow to reservoir "R" via fluid passageways 422 and 424. As before, container 400 is externally thread so that it can be locked in place within chamber 408 by means of the locking tabs 336d in the manner previously described.

With the reservoir "R" fully charged so as to distend membrane 201 to the outward position shown by the phantom lines in FIG. 26, the dispensing step can be commenced by piercing sleeve 449 with a suitably delivery spike assembly (not shown). This will permit the energy source or distended membrane 201 to move to a less distended configuration causing the diluent to flow outwardly of the reservoir via passageways 460 and into hollow needle 444. The diluent will then flow through porous plug 440a, through glass frit 244 and around, about and through the additive contained within chamber 432 of the adding means. the fluid mixture thus formed will then flow outwardly of the device via the delivery spike assembly.

FIG. 28 shows an alternate form of dispensing means, namely a luer lock assembly 470, which takes the place of the delivery spike assembly. In this alternate form of the invention, the structure of the device is substantially identical to that just described and like numbers are used to identify like components. However, the dispensing step is accomplished by connecting the delivery set to luer connector 470a and opening an externally located valve (not shown) so that the fluid mixture will flow from chamber 432 of the cartridge assembly through fluid passageway 472 provided in the luer lock assembly.

Turning now to FIGS. 29 and 29A, still another form of the invention is there shown. The apparatus here shown is similar to that shown in FIGS. 26 and 26A and like numbers have been used to identify like components. The major difference between the embodiment of the invention shown in these figures and that described in connection with FIGS. 26 and 26A resides in the fact that the energy source for expelling the fluid is totally different. More particularly, in this latest form of the invention, the distendable membrane 201 has been replaced with a deformable barrier like member 500 which forms an interface between the energy source and the fluid entering reservoir "R". Member 500 can be constructed of a number of materials, such as various elastomers, and is generally tubular in shape as is the previously described distendable membrane 201.

As best seen in FIG. 29, the important stored energy source is here provided in the form of an elastically deformable, cellular foam like expandable member 502 which is disposed within chamber 14 of the device in the manner shown in FIG. 29. Member 502 can be constructed from a wide variety of materials, including a number of flexible cellular polymers and foamed polymers. Materials that are particularly attractive for this application include polyurethane, latex foam rubber, cellular rubber, various polyolefin foams, PVC foams, epoxy foams, urea formaldehyde, silicon foam, fluropolymer foams, and other elastic syntactic foams and similar materials of a character well understood by those skilled in the art. Member 502 can be monolithic or it can be constructed from homogenous or nonhomogenous foam or laminates having the same or different characteristics. Similarly, barrier member 500 can be independent from member 502 or it can be either affixed thereto or integrally formed therewith.

In the operation of this latest embodiment of the invention, the piston 402 which moves within the reservoir 404 of the container is pierceable by a hollow needle 406 which is carried by a valve housing 407 disposed within the inlet chamber 408 of the support means. The reservoir "R" of the device is filled by urging container 400 telescopically inwardly of chamber 408 causing needle 406 to pierce piston 402 and causing the piston to move longitudinally of container 404. As container 400 moves inwardly of chamber 408, it is guided by guide means shown here as a cross-like guide member 414 which is carried by a longitudinally extending hollow column 416 and which includes four radially outwardly extending legs 414a the extremities of which guidingly engage the interior wall of container reservoir 404.

As before, fluid, such as diluent "D" flowing from reservoir 404 through needle 406 will cause a valve member 418, which is carried within a chamber 420 provided in housing 407, to move to the left and away from valve seat 407a permitting fluid to flow toward reservoir "R" via central passageway 422 provided in column 416. The fluid flowing through passageway 422 will flow under pressure through radially outwardly extending passageways 424 provided in support 410 and will impinge on deformable member 500 causing it to deform outwardly from the position shown on the solid lines to the position shown by the phantom lines in FIG. 29. As the deformable member is moved outwardly, sponge like member 502 will be correspondingly compressed to conform to the shape of the deformed barrier member 500 (see phantom lines in FIG. 29). In this instance, member 502 is both compressible and expandable so that during the dispensing step it will expand against barrier member 500 in a manner to urge the barrier member inwardly so as to force the diluent outwardly of the reservoir "R". In some instances, the sponge like member 502 can be disposed within chamber 14 in a prestressed configuration so that it will be automatically expandable at the desired time.

As was the case with the embodiment shown in FIG. 26, in this latest form of the invention, the adding means is disposed proximate the outlet of the device and comprises a sealed cartridge assembly 430 having an additive-containing chamber 432 for containing an additive generally designated by the numeral 434. Once again, 434 can be any material of the character defined in the preceding paragraphs. Cartridge 430 is closely receivable within an outlet chamber 437 provided in support 410 and has first and second ends 430a and 430b. End 430a is sealably closed by a septum 440 which is held in place by a crimp cap 442. Septum 440 is pierceable by a hollow needle 444 which is mounted on a transverse wall 410 of support 410. End 430b of the cartridge is closed by a closure assembly 447 which includes a pierceable sleeve 449 that is pierceable by a delivery spike of a character well known in the art. Closure assembly 447 is held in place by an annular crimp cap 450 which exposes a shield 449a which is superimposed over sleeve 449. Sleeve 449 can be constructed from a pierceable material such as rubber, which can be punctured by a conventional delivery spike to open a fluid flow path which communicates with chamber 432 of the adding means via porous plug 229 and a glass frit 230.

In this latest form of the invention, as was the case with the embodiment of FIG. 26, cartridge assembly 430 is inserted into outlet chamber 437 through an opening 452 provided in end wall 454 and a thread 456, provided on a cartridge overpackage 430a, is mated with a thread 458 provided on support 410. As the cartridge assembly is threadably mated with the support, needle 444 will penetrate septum 440 establishing fluid communication between chamber 432 of the cartridge assembly and reservoir "R" via hollow needle 444 and outlet passageways 460 provided in support 410.

After container 400 has been filled with a suitable first component such as a diluent "D", piston 402 is inserted into the open end of the container and sealing cap 464 (FIG. 27) is emplaced over the assemblage thus formed so as to maintain the first component in a sterile, sealed condition until time of use.

With the cartridge assembly positioned within chamber 437 in the manner shown in FIG. 26, tear-away cap 464 of the fluid container assembly 400 is removed and the container is inserted into the opening provided in end wall 300 of the housing 12. As the container assembly is urged to the left as viewed in FIG. 29, needle 406 will pierce plug 402 opening a fluid path between reservoir 404 and check valve chamber 420 of valve housing 407. Continued inward telescopic movement of the fluid container will cause the check valve to open permitting the diluent to flow toward reservoir "R" via fluid passageways 422 and 424. As before, container 400 is externally thread so that it can be locked in place within chamber 408 by means of the locking tabs 336d in the manner previously described.

With the reservoir "R" fully charged so as to deform member 500 into the outward position shown by the phantom lines in FIG. 29, energy source or member 502 will be correspondingly compressed so that, as before, the dispensing step can be commenced by piercing sleeve 449 with a suitably delivery spike assembly (not shown). This will permit the energy source to act on member 500 causing it to force the diluent outwardly of the reservoir via passageways 460 and into hollow needle 444. The diluent will then flow through porous plug 440a, through glass frit 244 and around, about and through the additive contained within chamber 432 of the adding means. the fluid mixture thus formed will then flow outwardly of the device via the delivery spike assembly.

Turning now to FIGS. 30 and 30A, a somewhat different form of the invention is there shown. The apparatus of this form of the invention is similar to that illustrated in FIGS. 25 and 25A and like numerals have been used to identify like components. Once again, the major difference between this latest embodiment and that shown in FIG. 25 resides in the character of the energy source which will presently be described. As in the earlier form of the invention, in using this latest embodiment, the drug vial or additive assemblage is first secured within the inlet chamber of the central support of the device and fluid is then introduced into the device to charge the reservoir by means of a separate cooperating diluent vial.

As best seen in FIG. 30, once again the housing 12 comprises a cylindrically shaped central portion 12a to which end plates 300 and 302 are connected to define an internal chamber 304. Support means in the form of a support 306 is disposed within chamber 304 and extends longitudinally thereof. However, in this embodiment, the elastomeric member 201 has been once again replaced with a deformable, generally tubular shaped member 550 which is connected to support 306 by suitable clamps 20. The construction and operation of deformable member 550 will be described in greater detail in the paragraphs which follow.

As before, support 306 is provided with an outlet chamber 310 and includes fluid passageways 312 leading to reservoir "R". Receivable within chamber 310 is a fluid dispensing means, shown here as a luer connector assembly 314, which includes a body portion 314a and a luer connector 314b. Receivable within body portion 314a is a filter means "F" for filtering fluid flowing from reservoir "R" toward the dispensing means.

The cartridge assembly 318 of the adding means of this form of the invention shown in FIG. 30 includes a chamber 320 which is sealed at either end by septums 322 and 324. As before, the septums can be constructed from a self-sealing, non-coring material such as silicone SEBS which can be sealably punctured by a hollow needle such as needle 326 which is mounted in a valve housing 328 carried within a chamber 330 provided in support 306. It is to be noted that the cartridge assembly is internally threaded while the valve housing 328 is provided with mating threads. With this construction, as the cartridge assembly 318 is inserted into the inlet chamber 332 of support 306 and is moved into a seated position, needle 326 will pierce septum 324 in the manner shown in FIG. 30. This opens fluid communication between the internal chamber 320 of the cartridge assembly and the reservoir "R".

Receivable over a tubular wall 306a which surrounds cartridge assembly 318 is a diluent container 336. Container 336, is of the same construction as previously described and operates in precisely the same manner.

In using the apparatus of this latest form of the invention, caps 345 and 347 which are provided at either end of the cartridge assembly are first removed as is vent cap 139. The cartridge assembly is then inserted into the open end of chamber 332 and is threadably mated with valve member 328. As the cartridge subassembly mates with member 328, hollow needle 326 will penetrate septum 324 of the cartridge assembly in the manner shown in FIG. 30.

With the cartridge assembly positioned within chamber 332 in the manner shown in FIG. 30, tear-away cap 343 of the fluid container assembly 336 is removed and the container is emplaced over tubular wall 306a. As the container assembly is urged to the left as viewed in FIG. 30, needle 341 will pierce septum 322 of the cartridge assembly opening a fluid path between reservoir 338 and the interior chamber 320 of the cartridge assembly. Continued telescopic movement of the fluid container over wall 306a will cause piston 340 to move inwardly of the fluid container forcing the diluent 339 through glass frit 244 and then around, about and through the additive disposed within chamber 320. The fluid mixture thus formed will flow through the inboard glass frit 230 and into hollow needle 326 causing a valve member 350, which is carried within a cavity 352 provided in member 328, to move to the left or open position. This, in turn, will permit the fluid mixture to flow into circumferentially spaced fluid passageways 351 provided in member 328 (FIG. 25A) and then into passageways 354 formed in support 306. The fluid flowing through passageways 354 will pressurally impinge barrier member 550 causing it to tend to move outwardly to the position shown by the phantom lines in FIG. 30.

A highly novel feature of the present invention resides in the stored energy source which here comprises an elastic, cellular foam like resilient sponge member 552. Member 552 which is disposed within chamber 14 of the device can be constructed from a wide variety of materials, including a number of flexible cellular polymers. Materials that are particularly attractive for this application include polyurethane, latex foam rubber, cellular rubber, various polyolefin foams, PVC forms, epoxy foams, urea formaldehyde, silicon foam, fluropolymer foams, and other elastic syntactic foams and similar materials of a character well understood by those skilled in the art. Member 552 can be monolithic or it can be constructed from homogenous or nonhomogenous foam or foam laminates having the same or different characteristic.

During the filling step, the fluid passing through passageways 354 will act on deformable member 550 causing it to correspondingly ompress sponge like member 552. As member 552 is compressed, internal stresses will be formed in this member which will tend to cause it to return to a less distended configuration. Accordingly, during dispensing of the fluid mixture from the device, the fluid mixture will be forced through passageways 312 by the energy source or sponge like member 552 acting on member 550 which moves from the outwardly distended position shown in the phantom lines to the position shown in the solid lines wherein it is disposed proximate the support means. As before, the mixture will then flow through filter "F" and outwardly of the device via the luer connector assembly 314. Filter "F" can, as before, also act as a flow rate control means.

The additives of the previously described embodiments of the invention can take various forms and, can be removably affixed to the additive presentation means in various ways to enable the use of separation techniques broadly defined by the term chromotography. Chromotography as used herein refers to a group of separation techniques which are characterized by a distribution of the molecules to be separated between two phases, one stationary and the other mobile. Affinity chromotography involves the use of biological interactions and contemplates the use of affinity chromotography supports through which the eluting fluid flow. In the embodiments of the invention described herein, the additive presentation means assumes the character of an affinity chromotography support to which various ligands are attached. In the practice of affinity chromotography techniques, one of the members of the pair in the interaction, the ligand, is immobilized on a solid phase, while the other, the counterligand (most often a protein), is absorbed from the extract that is passing the substrate during the manufacturing process. Importantly, affinity chromotography techniques can include the use of highly versatile azlactone functional compounds, such as azlactone functional beads, as well as the use of a wide variety of other media for activation and coupling chemistry. Examples of ligands that can be attached to the affinity supports include antibodies, enzymes, lectins, nucleic acids hormones and vitamins. Examples of important counterligands include antigens, virus, cells, cell surface receptors and the like. Chromotography and affinity chromotography techniques are described in detail in *Protein Purification* by Janson and Ryden, Copyright 1989 and reference should be made to this work to provide a working understanding of the techniques.

Polymeric azlactones are well known in the prior art. Their use in the production of homopolymers and co-polymers has been described in a number of patents. See for example, U.S. Pat. No. 3,488,327 (issued Jan. 6, 1970 to F. Kollinsky et al.); U.S. Pat. No. 3,583,950 (issued Jun. 8, 1971 F. Kollinsky, et al.); U.S. Pat. No. 4,304,705 (issued Dec. 8, 1981 to S. M. Heilmann, et al.); and U.S. Pat. No. 4,737,560 (issued Apr. 12, 1988 to S.M. Heilmann, et al.); and U.S. Pat. No. 5,013,795 issued May 7, 1991 to Coleman, et al.

Azlactones, or oxazolones, are cyclic anhydrides of N-acylamino acids and have been used extensively in organic synthesis. The formation of a five-membered azlactone of particularly useful functionality for immobilization purposes can be accomplished through the reaction of a carboxylate group with a-methyl alanine using a two-step process. (See *Immobilized Affinity Ligand Techniques*—Hermanson, Mallia and Smith Copyright 1992). One method of forming azlatone beads, the use of which has been previously mentioned herein, makes use of this process in the polymerization of monomers to first yield a carboxyl group on the matrix. In the second step, the azlactone ring is formed in anhydrous conditions through the use of a cyclization catalyst. Suitable cyclization agents that will drive this reaction include acetic anhydride, alkyl chloroformates, and carbondiimides. The process of forming these active groups and of making beaded polymeric supports containing them has been thoroughly described in patents assigned to 3M Corporation (U.S. Pat. Nos. 4,871,824 and 4,737,560). These support materials are now available under the tradename "Emphase". U.S. Pat. Nos. 5,045,615 and 5,013,795 which have been assigned to 3M Corporation also described recent advances in this technology.

As pointed out in the 3M Corporation U.S. Pat. No. 4,737,560, azlactone-functional polymer beads are useful reactive supports for the attachment of functional materials to provide novel adduct beads. The adduct beads are useful as complexing agents, catalysts, reagents, and as enzyme or other protein-bearing supports. The term "support" or affinity support" as used in this sense is usually understood to refer to a combination of (1) a ligand (usually of some known molecular configuration), that is firmly attached (e.g., immobilized), often by covalent means, and (2) a matrix (usually a solid insoluable substance). Azlactone support matrix materials and coupling chemistry is also of special interest because of its accessible matrix surface area and effective ligand diversity that can be attached to that surface.

U.S. Pat. No. 4,072,566 issued to Lynn on Feb. 7, 1978, and entitled "Immobilized Biologically Active Proteins" discloses a method of bonding enzymes or other biologically active proteins to an inorganic support material using p-phenylenediamine. The support materials disclosed as useful in the invention include siliceous materials, stannic oxide, titania, manganese dioxide and zirconia.

The functional support structure of the invention can take on the character of an affinity support and is uniquely constructed to permit enzymes or other biologically active proteins to be bound thereto for later removal. This is accomplished by treating functional support 477 in the manner disclosed in the prior art patents identified in the preceding paragraphs with a compound having selected reactive functional groups such as azlactone functional compounds. In this way complexing agents, catalysts and biological materials such as enzymes, proteins or other affinity absorbents, as well as biomacromolecules can be attached to the carrier for later removal and recovering.

When attaching certain biologically active proteins and other macro molecules, the use of spacer arms or leashes have been found to be very beneficial. Spacer arms or leashes are low-molecular-weight molecules that are used as intermediary linkers between a support material and an affinity ligand. Usually spacers consist of linear hydrocarbon chains with functionalities on both ends for each coupling to the support and ligand. First, one end of the spacer is attached chemically to the matrix using traditional immobilization chemistries; the other end is connected subsequently to the ligand using a secondary coupling procedure. The result is an immobilized ligand that sticks out from the matrix backbone by a distance equal to the length of the spacer arm chosen.

Figure 31B:
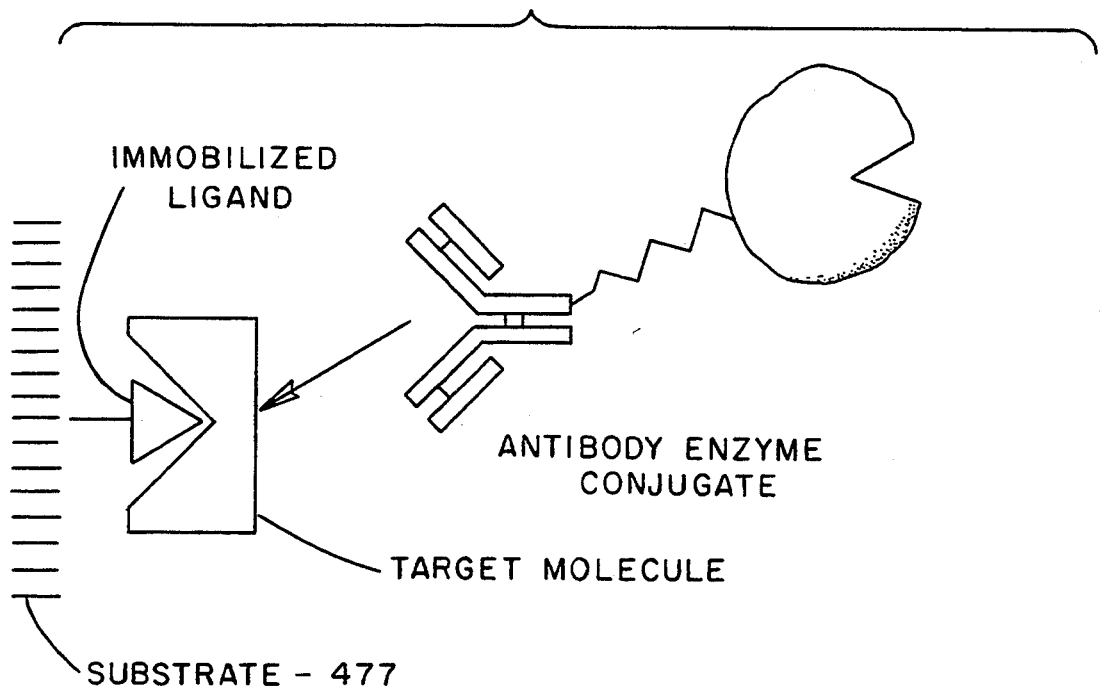

Referring to FIGS. 31A, 31B, 31C and 31D, the use of spacer arms to attach proteins and enzymes to the substrate is there schematically illustrated. The principal advantage of using a spacer arm is that it provides ligand accessibility to the binding site of a target molecule. When the target molecule is a protein with a binding site somewhat beneath its outer surface, a spacer is essential to extend the ligand out far enough from the matrix to allow interaction. As indicated in FIG. 31A, when the ligand binding site S is buried or in a pocket 475 located just below the surface of the protein P, a ligand L that is either below the surface of the support material 477 (upper portion) or a ligand L-1 that is attached directly to the surface (middle portion) cannot reach the level of the binding site S on an approaching protein molecule. The result may be weakened interaction or no binding at all. Accordingly, in these instances, spacer arm 479 is required to provide the ligand L-2 accessibility to the bind site of the protein molecule (lower portion of FIG. 61A). The details covering the use of spacer arms are fully set forth in Section 3.1.1 of the previously referred to work entitled *Immobilized Affinity Ligand Techniques*. This Section 3.1.1 is incorporated herein by reference.

Figure 31C:
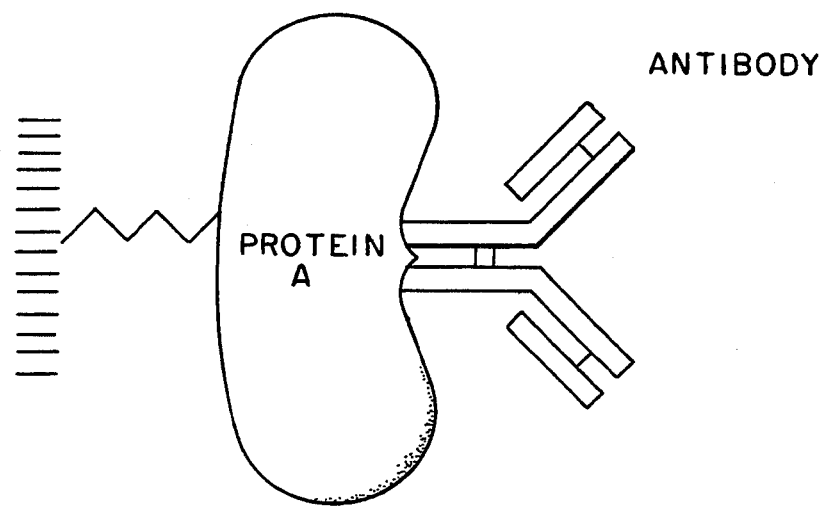
Figure 3D:
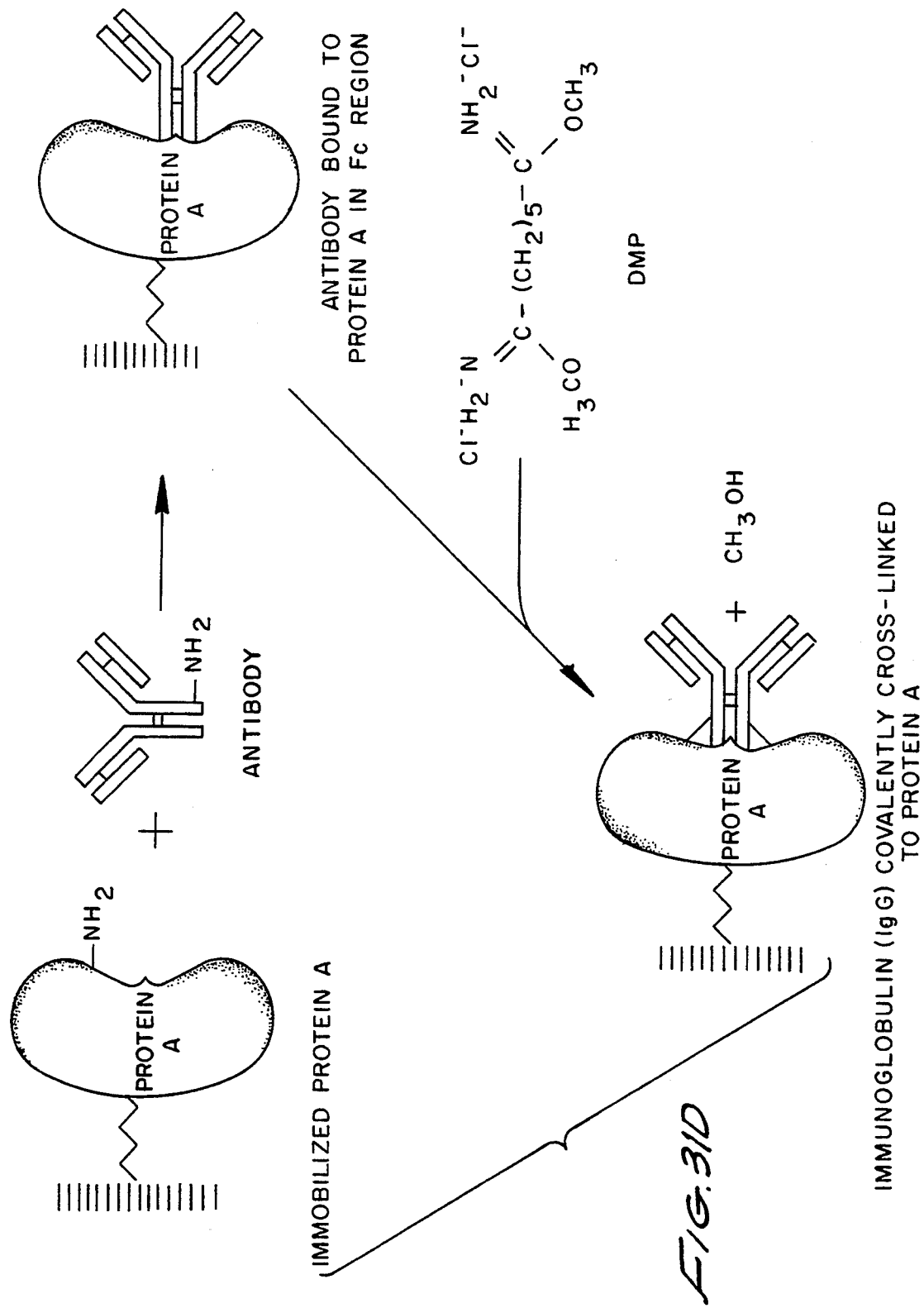

Turning now to FIGS. 31B, 31C and 31D, it is to be noted that immobilized protein A can be used to immobilize an antibody molecule by taking advantage of the natural affinity of protein A for immunoglobulins. Incubation of a specific antibody with protein A matrix will bind the antibody in the Fe region, away from the antigen binding sites. Subsequent cross-linking of this complex with DWP (dimethyl pimelimidate) yields a covalently attached antibody with the antigen binding sites facing outward and free to interact with antigen.

With rigid support materials, a spacer molecule may also provide greater flexibility, allowing the immobilized ligand to move into position to establish the correct binding orientation with a protein. The degrees of freedom that a hydrocarbon extender can provide are much greater than the movement possible within the polymeric backbone of a matrix.

The choice of spacer molecule can affect the relative hydrophilicity of the immediate environment of an immobilized ligand. Molecules containing long hydrocarbon chains may increase the potential for nonspecific hydrophobic interactions, especially when the affinity ligand is small and of low molecular weight. Selecting spacers that have more polar constituents, such as secondary amines, amide linkages, ether groups or hydroxyls will help keep hydrophobic effects at a minimum.

It is also important to consider the ionic effects a spacer molecule may impart to a gel. Spacers with terminal primary amine groups should be completely coupled with ligand or blocked by a nonrelevant molecule (e.g., acetic anhydride; see Section 3.1.1.9 of *Immobilized Affinity Ligand Techniques*) to eliminate the potential for creating a positive charge on the support. With small ligands, these residual charges can form a secondary environment that may cause considerable nonspecific interactions with proteins. The same holds true for spacers with terminal carboxylic groups. In general, a negatively charged spacer will cause less nonspecific protein binding than a positively charged one, but blocking excess remaining groups is still a good idea. A good blocking gent for use with carboxylic residues is ethanolamine, which leave a terminal hydroxyl group (See *Immobilized Affinity Ligand Techniques* for an expanded discussion of types of spacers and various immobilization and coupling protocols.)

As pointed out in *Protein Purification,* Janson and Ryden, Copyright 1989 which describes some alternate form of protein immobilization at Page 310:

"Ligand-protein interaction is often based on a combination of elactrostatic, hydrophobic and hydrogen bonds. Agents which weaken such interactions might be expected to function as effective non-specific eluants."

This work provides further teaching of the techniques described herein.

It is important to recognize that, as used in the present form of the invention, affinity supports are now capable of total binding capacity at a level that enables attachment to the support of additives in substantial amounts for subsequent release, recovery and infusion of beneficial agents in a manner which can therapeutically efficatious to a patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:
1. A fluid dispensing device comprising:
   (a) a housing having walls defining an internal chamber and support means for supporting a stored energy source within said internal chamber, said support means having a fluid inlet and a fluid outlet;
   (b) filling means for introducing fluid into said fluid inlet of said support means;
   (c) a generally tubular shaped elastomeric member connected proximate its ends of said support means, said elastomeric member having a central portion disposed within said internal chamber of said housing and overlaying said fluid inlet and said fluid outlet of said support means, said central portion of said elastomeric member being distendable by fluid flowing through said fluid inlet of said support means from a first position in proximity with said support means to second position; and
   (d) adding means carried by said support means for adding an additive to fluid introduced by said filling means, said adding means comprising container means for containing said additive.

2. A device as defined in claim 1 in which said container means comprises a container having an inlet and an outlet, said inlet being sealed by a first sealing means and said outlet being sealed by a second sealing means.

3. A device as defined in claim 2 in which said filling means includes a hollow needle connected to said support means, said hollow needle being in communication with said fluid inlet and said support means and being adapted to pierce said second sealing means of said chamber.

4. A device as defined in claim 2 in which said support means comprises an elongate support member having an inlet chamber and an outlet chamber.

5. A device as defined in claim 4 in which said container is receivable within said inlet chamber of said support member.

6. A device as defined in claim 4 in which said container is receivable within said outlet chamber of said support member.

7. A device as defined in claim 4 in which said additive comprises a beneficial agent.

8. A device as defined in claim 4 in which said additive comprises a biologically active material.

9. A device as defined in claim 4 in which said additive comprises a drug.

10. A fluid dispensing device comprising:
    (a) an elongate housing having walls defining an internal chamber;
    (b) a support connected to said housing, said support being disposed within said internal chamber and having a fluid inlet and a fluid outlet and first and second chambers;
    (c) filling means for introducing fluid into said fluid inlet of said support;
    (d) an elongate tubular shaped elastomeric member connected proximate its ends to said support, said elastomeric member having a central portion disposed within said internal chamber of said housing and overlaying said fluid inlet and said fluid outlet of said support said central portion of said elastomeric member being distendable by fluid flowing through said fluid inlet of said support from a first position in proximity with said support to a second position; and
    (e) adding means receivable within one of said first and second chambers of said support for adding an additive to fluid introduced by said filling means, said adding means comprising a container having an internal chamber, said additive being present within said internal chamber.

11. A device as defined in claim 10 in which said container includes an inlet and an outlet said inlet being sealed by a first sealing means and said outlet being sealed by a second sealing means.

12. A device as defined in claim 11 further including a hollow needle connected to said support proximate said first chamber, said hollow needle being adapted to pierce said second sealing means of said chamber.

13. A device as defined in claim 11 in which said filling means is adapted to introduce fluid into said container through said first sealing means.

14. A device as defined in claim 11 in which said inlet of said container is in communication with said outlet of said support.

15. A fluid dispensing device comprising:
    (a) a housing having walls defining an internal chamber;
    (b) a support connected to said housing, said support being disposed within said internal chamber and having:
        (i) a first fluid passageway having an inlet and an outlet;
        (ii) a second fluid passageway having an inlet and an outlet;
        (iii) filling means for introducing fluid into said inlet of said first fluid passageway; and
        (iv) dispensing means in communication with said fluid outlet of said second fluid passageway for dispensing fluid from said dispenser;
    (c) an elastomeric member connected proximate its ends to said support, said elastomeric member having a central portion disposed within said internal chamber of said housing and overlaying said fluid outlet of said first fluid passageway and said fluid inlet of said second fluid passageway, said central portion of said elastomeric member being distendable by fluid flowing through said fluid outlet of said first fluid passageway from a first position in proximity with said support to a second position; and (d) adding means disposed within one of said first and second fluid passageways for adding an additive to fluid flowing therethrough said adding means comprising a vial having first and second ends, a chamber disposed intermediate said first and second ends and first and second sealing means for sealing said first and second ends of said vial respectively.

16. A device as defined in claim 15 in which said additive is contained within said chamber of said vial.

17. A device as defined in claim 16 in which said additive comprises a beneficial agent.

18. A device as defined in claim 16 in which said additive comprises a biologically active material.

19. A device as defined in claim 16 in which said additive comprises a drug.

20. A fluid dispensing device comprising:

(a) a housing having walls defining an internal chamber and support means for supporting a stored energy source within said internal chamber, said support means having a fluid inlet and a fluid outlet;

(b) filling means for introducing fluid into said fluid inlet of said support means;

(c) a generally tubular shaped deformable member connected proximate its ends to said support means, said deformable member having a central portion disposed within said internal chamber of said housing and overlaying said fluid inlet and said fluid outlet of said support means, said deformable member being deformable by fluid flowing through said fluid inlet of said support means from a first position in proximity with said support means to second position in engagement with said stored energy source; and (d) adding means carried by said support means for adding an additive to fluid introduced by said filling means.

21. A device as defined in claim 20 in which said stored energy source comprises an expandable member adapted to act upon said deformable member to move it toward said first position.

22. A device as defined in claim 21 in which said expandable member comprises an elastically deformable member having a cellular structure.

23. A device as defined in claim 21 in which said expandable member comprises a foamed polymer.

24. A device as defined in claim 21 in which said expandable member comprises an elastomer.

25. A fluid dispensing device comprising:

(a) an elongate housing having a cylindrical wall and interconnected end walls defining an internal chamber;

(b) a support connected to said housing, said support being disposed within said internal chamber and having a fluid inlet and a fluid outlet and first and second chambers;

(c) filling means for introducing fluid into said fluid inlet of said support;

(d) an elongate tubular shaped deformable member connected proximate its ends to said support, said deformable member having a central portion disposed within said internal chamber of said housing and overlaying said fluid inlet and said fluid outlet of said support, said central portion of said deformable member being deformed by fluid flowing through said fluid inlet of said support from a first position in proximity with said support to a second position;

(e) an expandable member disposed intermediate said cylindrical wall of said housing and said deformable member and being adapted to act on said deformable member to tend to move said member toward said first position; and (f) adding means receivable within one of said first and second chambers of said support for adding an additive to fluid introduced by said filling means, said adding means comprising a container having an internal chamber, said additive being present on additive presentation means contained within said internal chamber.

26. A device as defined in claim 25 in which said adding means comprises a polymer.

27. A device as defined in claim 25 in which said additive comprises a beneficial agent.

28. A device as defined in claim 25 in which said additive comprises a biologically active material.

29. A device as defined in claim 25 in which said additive comprises a drug.

30. A device as defined in claim 25 in which said additive comprises an extended release drug.

31. An apparatus as defined in claim 25 in which said additive is substantially removable from said additive presentation means using affinity chromotography techniques.

32. An apparatus as defined in claim 25 in which a spacer arm is connected to said additive presentation means and in which a ligand is connected to said spacer arm.

33. An apparatus as defined in claim 25 including a ligand connected to said additive presentation means and a target molecule connected to said ligand.

34. An apparatus as defined in claim 33 in which an enzyme is connected to said target molecule.

35. An apparatus as defined in claim 33 in which target molecule is a protein.

36. A device as defined in claim 35 in which said container includes an inlet and an outlet, said inlet being sealed by a first sealing means and said outlet being sealed by a second sealing means.

37. A device as defined in claim 36 further including a hollow needle connected to said support proximate said first chamber, said hollow needle being adapted to pierce said second sealing means of said chamber.

38. A device as defined in claim 36 in which said filling means is adapted to introduce fluid into said container through said first sealing means.

39. A device as defined in claim 36 in which said inlet of said container is in communication with said outlet of said support.

* * * * *